United States Patent
Brockmeier et al.

(10) Patent No.: US 11,107,566 B2
(45) Date of Patent: Aug. 31, 2021

(54) SYSTEMS AND METHODS FOR COMMUNICATING A DOSE HISTORY REPRESENTING AN AVERAGE AND A VARIABILITY OF A DISTRIBUTION OF MEDICAMENT INJECTIONS

(71) Applicant: Novo Nordisk A/S, Bagsvaerd (DK)

(72) Inventors: Pete Brockmeier, Copenhagen V (DK); Henrik Bengtsson, Taastrup (DK); Tinna Bjoerk Aradottir, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 289 days.

(21) Appl. No.: 16/335,142

(22) PCT Filed: Sep. 21, 2017

(86) PCT No.: PCT/EP2017/073850
§ 371 (c)(1),
(2) Date: Mar. 20, 2019

(87) PCT Pub. No.: WO2018/060036
PCT Pub. Date: Apr. 5, 2018

(65) Prior Publication Data
US 2019/0279754 A1   Sep. 12, 2019

(30) Foreign Application Priority Data
Sep. 30, 2016   (EP) .................................. 16191727

(51) Int. Cl.
*G16H 80/00*   (2018.01)
*G16H 10/60*   (2018.01)
*G16H 20/17*   (2018.01)

(52) U.S. Cl.
CPC ............. *G16H 20/17* (2018.01); *G16H 80/00* (2018.01); *A61M 2205/52* (2013.01); *G16H 10/60* (2018.01)

(58) Field of Classification Search
CPC ......... G16H 20/17; G16H 80/00; G16H 10/60
See application file for complete search history.

(56) References Cited

U.S. PATENT DOCUMENTS 8,046,242 B1 *   10/2011   daCosta ................. G16H 10/60
                                                             705/2
2001/0056358 A1 *   12/2001   Dulong .................. G16H 40/63
                                                             705/2

(Continued)

FOREIGN PATENT DOCUMENTS

EP       2774641 A1     9/2014
WO    2015047570 A1     4/2015

(Continued)

OTHER PUBLICATIONS

Abbott's illustration of representing insulin administration data, obtained at https://freestyle.de/produkte/flash-glukose-messgeraet/software/, accessed around Sep. 29, 2016.

(Continued)

*Primary Examiner* — Michael Tomaszewski
*Assistant Examiner* — Jay M. Patel
(74) *Attorney, Agent, or Firm* — Wesley Nicolas

(57) ABSTRACT

Systems and methods for communicating a dose history configured for representing an average and a variability of a distribution of injections with a blood glucose regulating medicament applied by a subject with a treatment regimen. Past records are obtained from insulin pens applying the treatment regimen. Each record specifies an amount and type of medicament injected, the type being one of a blood glucose regulating medicament, and a timestamp. Assigning single-shape polygons (231) to each record, wherein single- (Continued)

shape polygons (231) is configured for visualizing a polygon (261) with a two-dimensional shape, in a displayed mode. The single-shape polygons are used to create a set of multi-shape data structures comprising corresponding multi-shape polygons (244), configured for visualizing a polygon (265) with a two-dimensional shape, in the displayed mode (260). The multi-shape polygons are configured to be displayed with an increasing intensity, depending on the number of overlapping single-shape polygons used to define the multi-shape polygon. The method also comprises communicating display data (247), comprising (i) the plurality of sets of medicament records, and (ii) the set of multi-shape data structures (240).

15 Claims, 10 Drawing Sheets

(56) References Cited

U.S. PATENT DOCUMENTS

| | | | |
|---|---|---|---|
| 2002/0040282 A1* | 4/2002 | Bailey | G16H 20/10 |
| | | | 702/188 |
| 2003/0172081 A1* | 9/2003 | Dulong | G16H 70/40 |
| 2004/0046020 A1* | 3/2004 | Andreasson | G07F 17/0092 |
| | | | 235/385 |
| 2005/0272640 A1 | 12/2005 | Doyle et al. | |
| 2006/0272652 A1 | 12/2006 | Stocker et al. | |
| 2009/0232804 A1* | 9/2009 | Lazarides | A61P 37/06 |
| | | | 424/133.1 |
| 2010/0324936 A1* | 12/2010 | Vishnubhatla | G16H 50/70 |
| | | | 705/3 |
| 2013/0079727 A1 | 3/2013 | Schildt et al. | |
| 2014/0068487 A1* | 3/2014 | Steiger | G06F 19/00 |
| | | | 715/771 |
| 2014/0206970 A1 | 7/2014 | Wesley et al. | |
| 2014/0244296 A1* | 8/2014 | Linn | G16H 40/20 |
| | | | 705/3 |
| 2014/0335082 A1* | 11/2014 | Dransfield | A61K 31/337 |
| | | | 424/133.1 |
| 2015/0093328 A1* | 4/2015 | Drummond | A61K 51/1234 |
| | | | 424/1.21 |
| 2016/0098848 A1* | 4/2016 | Zamanakos | A61B 5/14532 |
| | | | 345/440 |
| 2016/0232321 A1* | 8/2016 | Silverman | G16H 50/50 |
| 2017/0216524 A1* | 8/2017 | Haider | A61M 5/24 |

FOREIGN PATENT DOCUMENTS

| | | |
|---|---|---|
| WO | 2016007935 A2 | 1/2016 |
| WO | 2016019192 A1 | 2/2016 |

OTHER PUBLICATIONS

Bergenstal et al., "Recommendations for Standardizing Glucose Reporting and Analysis to Optimize Clinical Decision Making in Diabetes: The Ambulatory Glucose Profile," Diabetes Sci Technol, 2013, vol. 7, No. 2, pp. 562-578.

Doug Kanter, Insulin on Board—Data Rep Final Project, May 14, 2012.

Medtronic MiniMed. "CareLink Pro Report Reference Guide" 2010, 37 pages.

* cited by examiner

SYSTEMS AND METHODS FOR COMMUNICATING A DOSE HISTORY REPRESENTING AN AVERAGE AND A VARIABILITY OF A DISTRIBUTION OF MEDICAMENT INJECTIONS

CROSS-REFERENCE TO RELATED APPLICATIONS

This application is a 35 U.S.C. § 371 National Stage application of International Application PCT/EP2017/073850 (WO 2018/060036), filed Sep. 21, 2017, which claims priority to European Patent Application 16191727.3, filed Sep. 30, 2016, the contents of all above-named applications are incorporated herein by reference.

TECHNICAL FIELD

The present disclosure relates generally to systems and methods for communicating a dose history configured for representing an average and a variability of a distribution of injections with a blood glucose regulating medicament applied by a subject with a treatment regimen.

BACKGROUND

Type 2 diabetes mellitus is characterized by progressive disruption of normal physiologic insulin secretion. In healthy individuals, basal insulin secretion by pancreatic β cells occurs continuously to maintain steady glucose levels for extended periods between meals. Also in healthy individuals, there is prandial secretion in which insulin is rapidly released in an initial first-phase spike in response to a meal, followed by prolonged insulin secretion that returns to basal levels after 2-3 hours.

Insulin is a hormone that binds to insulin receptors to lower blood glucose by facilitating cellular uptake of glucose, amino acids, and fatty acids into skeletal muscle and fat and by inhibiting the output of glucose from the liver. In normal healthy individuals, physiologic basal and prandial insulin secretions maintain euglycemia, which affects fasting plasma glucose and postprandial plasma glucose concentrations. Basal and prandial insulin secretion is impaired in Type 2 diabetes and early post-meal response is absent. To address these adverse events, subjects with Type 2 diabetes are provided with insulin medicament treatment regimens. Subjects with Type 1 diabetes are also provided with insulin medicament treatment regimens. The goal of these insulin medicament treatment regimens is to maintain a desired fasting blood glucose target level that will minimize estimated risk of hypo- and hyper-glycaemia. In recent years subjects with Type 2 diabetes have also been treated with liraglutide, long-acting glucagon-like peptide-1 receptor agonist, as an injectable prescription medicine that may regulate and improve blood sugar, and it should be used along with diet and exercise.

Traditional insulin medicament delivery systems have included the use of pump systems that provide a frequent recurrent dosage of insulin medicament. Additional types of delivery systems have been developed, such as insulin pens, which can be used to self-administer insulin medicament treatment regimens in the form of less frequent insulin medicament injections or injections with other types of blood glucose regulating medicaments. A common approach to Type 1 and Type 2 diabetes using such delivery systems is to inject a single short acting insulin medicament (bolus) dosage in a prescribed insulin regimen for the subject in response to or in anticipation of a meal event. In such approaches, the subject injects the short acting insulin medicament dosage shortly before or after one or more meals each day to lower glucose levels resulting from such meals.

A recent development for injection devices, is the development injector systems which are capable of storing dose history (dose size and time), and subsequently sending historical dose data to a mobile phone or computer system. There is a need to effectively visualize this data. The data can be visualized in combination with historical glucose data, in order to draw conclusions about the appropriateness of the dose regimen for desired glucose control.

A common method of representation of glucose data for viewing by a health care provider or patient is the Ambulatory Glucose Profile (AGP), which was developed by clinicians to demonstrate the median level of glucose control as well as an index of variability in control at each hour of a "standard day." The ability to show both an average glucose value, as well as variability, is an important element of AGP. If the average glucose is higher than the target range, but the variability is also very high, it may be dangerous to address tis by simply increasing insulin dose size, as hypoglycaemia could result. Furthermore, it is known that the existence of high variability in blood glucose can be detrimental, even with an average within range. US 2014/0206970 discloses a method of generating an ambulatory glucose profile window including a graphical display of the glucose data across a modal day.

The visual display presents a modal day (also called standard day, average day) in which all collected data over multiple days are collapsed and plotted according to time (without regard to date) as if they occurred over 24 h, starting and ending at midnight. Smoothed curves representing the median (50th), 25th, and 75th (IQR) and 10th and 90th frequency percentiles define the 24 h AGP, as further described in Journal Diabetes Science Technology, March 2013, Volume 7, Issue 2: pages 562-578.

While clinicians can use this type of visualized data to make some conclusions about the suitability of the current insulin regime being used by the patient, the glucose curve is the output of a number of inputs. An important input, for a diabetic patient, is injections with blood glucose regulating medicaments.

Doug Kanter represented in a final project for the Data Representation class at ITP, an insulin on board profile showing the accumulated insulin on board delivered by an insulin pump and the corresponding glucose data. The project was published on:
https://dougkanter.wordpress.com/2012/05/14/insulin-on-board-data-rep-final-project/. The link was retrieved on 29 Sep. 2016.

Medtronic represented in a Report Reference Guide for CareLink pro, which is a therapy management software for diabetes, that the basal and the bolus infusion rate can be shown along with glucose data. The software is developed for handling insulin data from a pump.

The guide was published on:
https://www.medtronicdiabetes.com/sites/default/files/library/download-library/user-guides/carelink-v3_0/en-_carelink_pro_report_ref_guide.pdf. The link was retrieved on 29 Sep. 2016.

WO 2015/047570 discloses a system for delivering and recording a dose of a medicament to a patient, WO 2016/007935 discloses methods, systems and devices for administering a medicament to a patient. The system includes an injection pen device in wireless communication with a mobile communication device. The device comprises an electronics unit in communication with a sensor unit to process a detected dispensed dose and time data associated with a dispensing event, and to wirelessly transmit the dose data to a user's device. The mobile communication device provides a software application to provide the user with health information using the processed data.

EP 2774641 B1 discloses an arrangement for administering a selected dosage of insulin. The arrangement comprises a sensor for contactless sensing of an adjusted dose. US 2013/0079727 discloses an application assembly comprising means for determining and registering the time and/or date and means for determining the selected and administered dosage. The date and/or the time may be transmitted to a receiver by means of a transmitter together with the signal of the applied amount of the medicament. The transmission can e.g. be via Bluetooth to a cell phone. The assembly may be provided with a display for showing warnings, transmission data, status information and the like. This facilitates the handling.

US 2006/0272652 identifies a need to provide both diabetes patients and medical professionals with an interactive visual teaching tool that illustrates the effects of certain intakes and events on blood glucose levels and present this information in an easy-to-read and understandable user format. The document discloses a screen where a doctor manipulate and view screen has been displayed. The doctor manipulate and view screen includes an insulin delivery graph, a carbohydrate ingested graph, and a blood glucose level graph. The timeframe graphed in the doctors manipulate and view screen being in a modal mode is one day. Each of the days having readings displayed in the doctor manipulate and view screen are displayed in a different color or with a different width/typeface. Illustratively, one line represents Monday, a second line represents Tuesday, and a third line represents Wednesday. This view allows a doctor utilizing the virtual patient software to see multiple days of readings for a specific patient and to determine if a time frame specific problem is occurring. The insulin delivery graph is illustrated by rectangles indicating time of injection and magnitude of injected medicament.

WO 2016/019192 discloses an electronic insulin delivery device receiving glucose data from a glucose monitor and sets a bolus dose amount. The device may take the form of an insulin pen with automatic priming and accurate dosing provided by a motor in connection with an encoder. The device may communicate with and be controlled by a smart phone device. The smart phone device provides a user interface to receive user data including patient weight, insulin to carbohydrate ratio and exercise factor, and to send instructions to the device, including dose amount. The dose amount is determined taking into account glucose level and trend, and other factors. The delivery device may be in continuous communication with the glucose monitor and smart phone to provide for near real-time adjustments in glucose treatment. Glucose data, insulin injection data, and other relevant data may be stored and accessible to interested parties.

US 2014/0068487 discloses methods for visualizing correlations between blood glucose data and events. The methods and apparatus can include presenting an event analysis window on a display communicatively coupled to one or more processors. The event analysis window can include an event type control positioned within the event analysis window and a graphical window positioned within the event analysis window. A plurality of continuous glucose monitoring traces can be plotted within the graphical window. Bolus icons each indicative of a bolus amount and a bolus time can be presented within the event analysis window. Each of the bolus icons can include a bolus indication object that is aligned with the bolus ordinate axis within the graphical window, a bolus time indication object that is aligned with the time abscissa axis within in the graphical window, and a bolus symbol that is presented outside of the graphical window.

Having regard to the above, it is an object of the present invention to provide a device, a system and a method to facilitate extraction, structuring and communication of technical information on how the automatically obtained events are distributed, and thereby enabling the communication of a dose history configured for representing an average and a variability of a distribution of automatically obtain injection events with a blood glucose regulating medicament applied by a subject with a treatment regimen, and thereby improving the possibility of understanding how the treatment regimen is applied.

It is a further object of the invention to provide a device or a system and a method for, in combination with a dose history, further communicating glucose measurements of the subject, and thereby improving the possibility of understanding the relation between glucose data and the distribution of injection event within a time period.

It is a further object of the invention to provide a device or a system and a method for, in combination with a dose history, further communicating a life-style event history representing an average and a variability of a distribution of life-style related events within the time course, which the subject has engaged in, and thereby improving the possibilities of understanding the relation between the events the subject engages in.

SUMMARY

In the disclosure of the present invention, embodiments and aspects will be described, which will address one or more of the above objects or which will address objects apparent from the below disclosure as well as from the description of exemplary embodiments.

In a first aspect is provided, a device for communicating a dose history configured for representing an average and a variability of a distribution of injections with a blood glucose regulating medicament applied by a subject with a treatment regimen;

the device comprises one or more processors and a memory, the memory storing instructions that, when executed by the one or more processors, perform a method of:

obtaining a first data set from one or more injection devices used by the subject to apply the treatment regimen, the first data set comprising a plurality of medicament records taken over a time course, each respective medicament record in the plurality of medicament records comprising:

(i) a respective medicament injection event including an amount of medicament injected into the subject using a respective injection device in the one or more injection devices, (ii) a corresponding electronic injection event timestamp within the time course that is automatically generated by the respective injection device upon occurrence of the respective medicament injection event;

wherein each of the medicament records are assigned:
a corresponding single-shape data structure, configured for representing a single injection in the distribution of injections, in a displayed mode, wherein the single-shape data structure comprises:
(i) a corresponding single-shape polygon, configured for visualizing a polygon with a two-dimensional shape, in the displayed mode, wherein the single-shape polygon is configured to be displayed with:
a first length extending in the first dimension, and with first a coordinate according to the first dimension, wherein (i) the first length is having a fixed value, or (ii) wherein the first length is variable and represents a duration wherein the medicament relating to the respective medicament injection event is still active, and
a second length extending in the second dimension, and with a second coordinate according to the second dimension, wherein (i) the second length is having a fixed value, or (ii) wherein the second length is variable and represents an amount of injected medicament, or (iii) wherein the second length is variable and represents an amount of active medicament remaining from the injected amount of medicament;
(ii) a corresponding first intensity indicator, configured for displaying a first visual property of the single-shape polygon, in the displayed mode;
creating a plurality of consecutive time windows within the time course, wherein each time window is of the same fixed duration,
for each respective time window, creating a set of medicament records, and thereby creating a plurality of sets of medicament records, wherein each respective set of medicament records comprises a number of medicament records from the first data set, and wherein each respective medicament record within the respective set of medicament records have a timestamp in the respective time window;
for each respective medicament record, within each set of medicament records of the plurality of sets of medicament records, assigning a corresponding relative time being the relative time within the time window, whereby the plurality of sets of medicament records represents the distribution of injections;
for each respective set of medicament records, superimposing the single-shape polygon from each of the medicament records in the respective set of medicament records, wherein the single-shape polygon is superimposed according to the first dimension being the relative time and the second dimension being the amount of injected medicament, wherein an interval along the first dimension is defined by the fixed duration of the time window, and whereby two or more superimposed single-shape polygons may overlap within the interval;
responsive to identifying two or more superimposed overlapping single-shape polygons:
creating a set of multi-shape data structures, comprising a number of multi-shape data structures configured for representing the average and the variability of the distribution of injections, in a displayed mode,
for each multi-shape data structure:
(i) creating a corresponding subset of overlapping single-shape polygons, wherein the subset of overlapping single-shape polygons define a corresponding subset of single-shape data structures,
(ii) calculating a corresponding multi-shape polygon, configured for visualizing a polygon with a two-dimensional shape and according to the first and the second dimension, in the displayed mode, wherein the multi-shape polygon is defined by the overlap between the single-shape polygons of the corresponding subset of overlapping single-shape polygons, which corresponds to the subset of single-shape data structures,
(iii) calculating the number of elements in the subset, being the number of overlapping single-shape data structures in the subset of overlapping single shape polygons,
(iv) calculating a corresponding second intensity indicator, configured for displaying the first visual property of the multi-shape polygon, in the displayed mode, wherein the second intensity indicator is an increasing function of the number of elements in the subset; and
communicating display data, wherein the display data comprises:
(i) the plurality of sets of medicament records, and
(ii) the set of multi-shape data structures; and wherein the communication is directed to (i) the subject or (ii) to a health care provider for providing the dose history representing the average and the variability of the distribution of the injections.

Hereby is provided a multi-shape data structure comprising the functional data structuring the technically extracted information of how the automatically obtained timestamps are distributed, and thereby enabling the technical information to be communicated in a structured way. The multi-shape data structure comprising a multi-shape polygon can be calculated independently of any cognitive content of the single-shape polygons, as the coordinates and the form of the single-shape polygons are automatically provided. The multi-shape data structure can be calculated in order to enable the internal operation of the device with a view to facilitate extraction, structuring and communication of technical information irrespective of the cognitive information that it also provides, i.e., the technical information or data is communicated in the form of a data structure, and it can be communicated to the subject or the user irrespective of the cognitive content and whether the cognitive content is perceived by the subject or the user. In order to describe the significance between the technical information and the cognitive content of the data, it is believed that the cognitive content of the data structure, probably, only will be perceived by the subject when it is graphically interpreted on a display in the form of single-shape and multi-shape polygons, which also visually illustrates the technically determined intensity indicators. The time stamped event specifying the amount of blood glucose regulating medicament is automatically obtained in the sense, that the subject or user of the injection device is not required to perform an active step in order to obtain an electronic or digital time stamp and/or an electronic or digital amount of blood glucose regulating medicament. These data are automatically generated by the injection device upon application of injection, i.e., the injection is applied by the subject or user in order to expel an amount of medicament, but the generation of data is provided irrespective of the users intention, when he or she uses the device. By this technical configuration is provided a device or a system for communicating a dose history for representing an average and a variability of a distribution of injections with a blood glucose regulating medicament applied by a subject with a treatment regimen. In this way a user with the present device will be able to identify an average of the distribution by identified the position for the most intensely represented polygons, and at the same time he will be able to identify the variation by looking at the relative distance from individual polygons to the center of the most intensely represented polygons.

As appears the single-shape polygon is configured to be displayed with a first length extending in the first dimension, and a second length extending in the second dimension. In some alternatives the first length is having a fixed value, and in other alternatives, the first length is variable and represents a duration wherein the medicament relating to the respective medicament injection event is still active. In this case the duration can have a begin time stamp and an end time stamp indicating the active period of the medicament. Similarly, in some alternatives the second length extending in the second dimension, is having a fixed value or is variable and represents an amount of injected medicament or an amount of active medicament remaining from the injected amount of medicament. In embodiments, where the first length is variable and the second length is variable and represents the amount of active medicament remaining from the injected amount of medicament, polygons overlapping within the time course can furthermore be aggregated in order to represent the total insulin on board.

In a further aspect, the memory is storing a medicament duration of action profile for the blood glucose regulating medicament that is characterized by a duration of the blood glucose regulating medicament. The duration of action profile may be used by the processor for estimating the first length of the single shape polygon, when the first length is variable and represents a duration wherein the medicament relating to the respective medicament injection event is still active. Similarly, the duration of action profile may be used for estimating the second length, in the case where it is variable and represents an amount of active medicament remaining from the injected amount of medicament.

In some alternatives the treatment regimen comprises a bolus insulin medicament dosage regimen with a short acting insulin medicament and a basal insulin medicament dosage regimen with a long acting insulin medicament.

In a further aspect of the invention, the device further comprises a display, and the step of communicating display data further comprises: displaying the display data in a first coordinate system on the display, wherein a first coordinate axis is defined by the first dimension, and the second coordinate axis is defined by the second dimension. Each respective medicament record, in each respective set of medicament records, in each of the plurality of sets of medicament records, is displayed by arranging the corresponding single-shape polygon in the first coordinate system according to the corresponding relative time and the corresponding amount of medicament, and the visual property of the single-shape polygon has been defined by the corresponding first intensity indicator. In addition, each respective multi-shape data structure, in the set of multi-shape data structures, is displayed by arranging the corresponding multi-shape polygon in the first coordinate system, according to a position defined by the subset of overlapping single-shape polygons, and wherein the first visual property of the multi-shape polygon has been defined by the corresponding second intensity indicator.

Hereby is provided dose history communication device, which enables the user to view the communication of the device display.

In a further aspect, each respective medicament record in the plurality of medicament records further comprises: a corresponding type of medicament injected into the subject. In addition, the single-shape data structure corresponding to the respective medicament record further comprises a corresponding type of medicament indicator, configured for displaying a second visual property of the single-shape polygon, and thereby indicating the type of medicament injected into the subject. Furthermore, each of the single-shape data structures within the corresponding subset of single-shape data structures are having the same type of medicament indicator, thereby indicating that they relate to injections with the same type of medicament. In addition, each multi-shape data structure within the set of multi-shape data structures further comprises a second type of medicament indicator defined by the type of medicament indicator of the corresponding subset of single-shape data structures, and wherein the second type of medicament indicator, is configured for displaying the second visual property of the multi-shape polygon, and thereby indicating the type of medicament injected into the subject, whereby the set of multi-shape data structures is further configured for representing distributions relating to injections with different types of medicament.

Hereby, is provided display data that enables a user to view injections with different type of drugs in a consistent way.

In a further aspect, the device further comprises a display, and the step of communicating display data further comprises: displaying the display data in a first coordinate system on the display, wherein a first coordinate axis is defined by the first dimension, and the second coordinate axis is defined by the second dimension. In addition, each respective medicament record, in each respective set of medicament records, in the plurality of sets of medicament records, is displayed by arranging each of the single-shape polygons corresponding to the respective medicament record in the coordinate system according to the corresponding relative time and the corresponding amount of medicament, and wherein the first visual appearance has been defined by the first intensity indicator and the second visual appearance has been defined by the first type of medicament indicator, wherein both indicators are corresponding to the respective medicament record. Furthermore, each respective multi-shape data structure, in the set of multi-shape data structures, is displayed by arranging each of the multi-shape polygons corresponding to the respective multi-shape data structure in the coordinate system, according to a position defined by the subset of overlapping single-shape polygons, and wherein the first visual appearance has been defined by the second intensity indicator and the second visual appearance has been defined by the second type of medicament indicator.

Hereby is provided dose history communication device, which enables the user to view the communicated display data on the device display, and wherein the communication can be viewed for different types of medicaments.

In a further aspect, the display further comprises a second coordinate system comprising a first axis and a second axis, and wherein the second coordinate system represents an average and a variability of a distribution based on glucose data obtained within the time course. In addition, for the first coordinate system, the second axis represents the amount of injected medicament, and wherein, for the second coordinate system, the second axis represents a blood glucose concentration. Furthermore, the first axis of both coordinate systems represent the time and are defined within the interval defined by the time window, and the first axis of both coordinate systems have been arranged in parallel on top of each other or with an off-set in the direction of the second axis. In addition, the second axis of both coordinate systems have been arranged in parallel.

Hereby is provided a dose history communication device, which enables the user to view the communication on the device display, and wherein the display allows a user to observe correlations between the distribution of injections and blood glucose measurements.

For some alternatives the single-shape polygon is configured for visualizing a polygon with a two-dimensional shape defining a circle, and wherein the second length is having a fixed value.

In a further aspect the method further comprises: obtaining a second data set, wherein the second data set comprises a plurality of autonomous glucose measurements of the subject within the time course and, for each respective autonomous glucose measurement in the plurality of autonomous glucose measurements, a glucose measurement timestamp representing when the respective measurement was made; and for each respective time window, creating a set of glucose measurements, and thereby creating a plurality of sets of glucose measurements, and wherein each glucose measurement within the respective set of glucose measurements have a timestamp in the respective time window;

for each respective glucose measurement, associating a corresponding relative time being the relative time within the time window, whereby the plurality of sets of glucose measurements are representing a distribution of glucose measurements within the time window;

calculating, for the plurality of sets of glucose measurements, the average and the variability as a function of the relative time, wherein the display data further comprises the plurality of sets of glucose measurements, the corresponding relative time, and the calculated average and the variability as a function of the relative time.

In a further aspect, the dose history communication device is further adapted for communicating a life-style event history representing an average and a variability of a distribution of life-style related events within the time course, which the subject has engaged in, wherein the method further comprises:

obtaining a third data set from one or more wearable life-style measurement devices used by the subject to acquire life-style data, the third data set comprises a plurality of life-style data records over the time course, each respective life-style data record in the plurality of life-style data records comprises:
(i) a respective life-style event,
(ii) a corresponding electronic life-style event timestamp within the time course that is automatically generated by the respective life-style measurement device upon occurrence of the respective life-style related event, or by user actuation of the respective life-style measurement device, or a begin timestamp and an end timestamp indicating the beginning and the ending time of the life-style event engaged in by the subject;

wherein each of the life-style data records are assigned:
a corresponding single-shape life-style data structure, configured for representing a single event in the distribution of life-style related events, wherein the single-shape life-style data structure comprises:
(i) a corresponding single-shape life-style polygon, configured for visualizing a polygon with a two-dimensional shape in the displayed mode, wherein the single-shape life-style polygon is configured to be displayed with:
a first length extending in the first dimension, wherein the first length is having a fixed value, or is representing a duration of the life-style event the subject engaged in based on a response to an indication of that a begin time stamp and an end timestamp has been recorded, and
a second length extending in the second dimension;
(ii) a corresponding first intensity indicator, configured for displaying a first visual property of a single-shape life-style polygon, in the displayed mode; for each respective time window, creating a set of life-style data records, and thereby creating a plurality of sets of life-style data records, wherein each respective set of life-style data records comprises a number of life-style data records from the third data set, and wherein each respective life-style data record within the respective set of life-style data records have a life-style event timestamp in the respective time window;

for each respective life-style data record, within each set of life-style data records of the plurality of sets of life-style data records, assigning a corresponding relative life-style time being the relative time within the time window, whereby the plurality of sets of life-style data records represents the distribution of life-style related events;

for each respective set of life-style data records, superimposing the single-shape life-style polygon from each of the life-style data records in the respective set of life-style data records, wherein the single-shape life-style polygon is superimposed according to the first and the second dimension, wherein an interval along the first dimension is defined by the fixed duration of the time window, and whereby two or more superimposed single-shape life-style polygons may overlap within the interval;

responsive to identifying two or more superimposed overlapping single-shape life-style polygons:

creating a set of multi-shape life-style data structures, configured for representing the average and the variability of the distribution of life-style related events, in a displayed mode, for each multi-shape life-style data structure:
(i) creating a corresponding subset of overlapping single-shape life-style polygons, wherein the subset of overlapping single-shape life-style polygons define a corresponding subset of single-shape life-style data structures,
(ii) calculating a corresponding multi-shape life-style polygon, configured for visualizing a polygon with a two-dimensional shape, in the displayed mode, wherein the multi-shape life-style polygon is defined by the overlap between single-shape life-style polygons of the corresponding subset of overlapping single-shape life-style data structures,
(iii) calculating the number of elements in the subset, being the sum of overlapping single-shape life-style data structures in the subset of overlapping single shape life-style polygons,
(iv) calculating a corresponding second life-style intensity indicator, configured for displaying a first visual property of the multi-shape life-style polygon, in the displayed mode, wherein the second life-style intensity indicator is an increasing function of the number of single-shape life-style polygons. The display data further comprises: the plurality of sets of life-style data records, and the set of multi-shape life-style data structures (340). The communication is directed to (i) the subject or (ii) to a health care provider for providing the life-style event history representing the average and the variability of the distribution of the life-style related events.

In a further aspect, each of the life-style data records in the plurality of life-style data records further comprises: a quantity of impact representing the influence imposed by the life-style event on the subject's blood glucose level. In addition, the corresponding single-shape life-style polygon is further configured to be displayed with: a second length extending in the second dimension, wherein the second length is having a fixed value or is variable and represents the quantity of impact representing the influence on the subject's blood glucose level, whereby the set of multi-shape life-style data structures is further configured for representing distributions relating to quantifiable life-style events.

In a further aspect, each of the life-style data records in the plurality of life-style data records further comprises: a corresponding type of life-style event representing the type of event the subject engaged in. In addition, the corresponding single-shape life-style data structure further comprises: a corresponding first type of life-style event indicator, configured for displaying a second visual property of the single-shape life-style polygon, and thereby indicating the type of life-style event engaged in by the subject. Each of the single-shape life-style data structures within the corresponding subset of single-shape life-style data structures are having the same type of life-style event indicator, thereby indicating that they relate to the same type of life-style event engaged in by the subject. Each multi-shape life-style data structure within the set of multi-shape life-style data structures further comprises a second life-style event indicator defined by the type of life-style event indicator of the corresponding subset of single-shape life-style data structures. The second type of life-style event indicator, is configured for displaying a second visual property of the multi-shape life-style polygon, and thereby indicating the type of life-style event, which the subject has engaged in, whereby the set of multi-shape life-style data structure is further configured for representing distributions relating to different types of life-style events.

Hereby, is provided display data that enables a user to view a distribution of injections along with distributions of other events that may influence the blood glucose level.

In some alternatives the treatment regimen comprises a GLP-1 receptor agonist dosage regimen, with a medicament comprising a GLP-1 receptor agonist.

In a further aspect the invention relates to a method for communicating a dose event history representing an average and a variability of a distribution of injections with a blood glucose regulating medicament applied by a subject with a treatment regimen:

using a device comprising one or more processors and a memory, the memory storing instructions that, when executed by the one or more processors, perform a method of:

obtaining a first data set from one or more injection devices used by the subject to apply the treatment regimen, the first data set comprising a plurality of medicament records over a time course, each respective medicament record in the plurality of medicament records comprising:

(i) a respective medicament injection event including an amount of medicament injected into the subject using a respective injection device in the one or more injection devices, (ii) a corresponding electronic injection event timestamp within the time course that is automatically generated by the respective injection device upon occurrence of the respective medicament injection event;

wherein each of the medicament records are assigned:

a corresponding single-shape data structure, configured for representing a single injection in the distribution of injections, in a displayed mode, wherein the single-shape data structure comprises:

(i) a corresponding single-shape polygon, configured for visualizing a polygon with a two-dimensional shape, in the displayed mode, wherein the single-shape polygon is configured to be displayed with:

a first length extending in the first dimension, wherein the first length is having a fixed value, and a second length extending in the second dimension, wherein the second length is having a fixed value or is variable and represents an amount of injected medicament;

(ii) a corresponding first intensity indicator, configured for displaying a first visual property of the single-shape polygon, in the displayed mode;

creating a plurality of consecutive time windows within the time course, wherein each time window is of the same fixed duration, for each respective time window, creating a set of medicament records, and thereby creating a plurality of sets of medicament records, wherein each respective set of medicament records comprises a number of medicament records from the first data set, and wherein each respective medicament record (222) within the respective set of medicament records have a timestamp in the respective time window;

for each respective medicament record, within each set of medicament records of the plurality of sets of medicament records, assigning a corresponding relative time being the relative time within the time window, whereby the plurality of sets of medicament records represents the distribution of injections;

for each respective set of medicament records, superimposing the single-shape polygon from each of the medicament records in the respective set of medicament records, wherein the single-shape polygon is superimposed according to the first and the second dimension, wherein an interval along the first dimension is defined by the fixed duration of the time window, and whereby two or more superimposed single-shape polygons may overlap within the interval;

responsive to identifying two or more superimposed overlapping single-shape polygons:

creating a set of multi-shape data structures, comprising a number of multi-shape data structures configured for representing the average and the variability of the distribution of injections, in a displayed mode, for each multi-shape data structure:

(i) creating a corresponding subset of overlapping single-shape polygons, wherein the subset of overlapping single-shape polygons define a corresponding subset of single-shape data structures, (ii) calculating a corresponding multi-shape polygon, configured for visualizing a polygon with a two-dimensional shape, in the displayed mode, wherein the multi-shape polygon is defined by the overlap between the single-shape polygons of the corresponding subset of overlapping single-shape polygons, which corresponds to the subset of single-shape data structures, (iii) calculating the number of elements in the subset, being the number of overlapping single-shape data structures in the subset of overlapping single shape polygons, (iv) calculating a corresponding second intensity indicator, configured for displaying the first visual property of the multi-shape polygon, in the displayed mode, wherein the second intensity indicator is an increasing function of the number of elements in the subset; and communicating display data, wherein the display data comprises:
(i) the plurality of sets of medicament records, and
(ii) the set of multi-shape data structures; and wherein the communication is directed to (i) the subject or (ii) to a health care provider for providing the dose history representing the average and the variability of the distribution of the injections.

In a further aspect is provided a computer program comprising instructions that, when executed by one or more processors, perform the method of:

obtaining a first data set from one or more injection devices used by the subject to apply the treatment regimen, the first data set comprising a plurality of medicament records taken over a time course, each respective medicament record in the plurality of medicament records comprising:
(i) a respective medicament injection event including an amount of medicament injected into the subject using a respective injection device in the one or more injection devices,
(ii) a corresponding electronic injection event timestamp within the time course that is automatically generated by the respective injection device upon occurrence of the respective medicament injection event;

wherein each of the medicament records are assigned:
a corresponding single-shape data structure, configured for representing a single injection in the distribution of injections, in a displayed mode, wherein the single-shape data structure comprises:
(i) a corresponding single-shape polygon, configured for visualizing a polygon with a two-dimensional shape, in the displayed mode, wherein the single-shape polygon is configured to be displayed with:
a first length extending in the first dimension, and with first a coordinate according to the first dimension, wherein (i) the first length is having a fixed value, or (ii) wherein the first length is variable and represents a duration wherein the medicament relating to the respective medicament injection event is still active, and
a second length extending in the second dimension, and with a second coordinate according to the second dimension, wherein (i) the second length is having a fixed value, or (ii) wherein the second length is variable and represents an amount of injected medicament, or (iii) wherein the second length is variable and represents an amount of active medicament remaining from the injected amount of medicament;

(ii) a corresponding first intensity indicator, configured for displaying a first visual property of the single-shape polygon, in the displayed mode;

creating a plurality of consecutive time windows within the time course, wherein each time window is of the same fixed duration,
for each respective time window, creating a set of medicament records, and thereby creating a plurality of sets of medicament records, wherein each respective set of medicament records comprises a number of medicament records from the first data set, and wherein each respective medicament record within the respective set of medicament records have a timestamp in the respective time window;

for each respective medicament record, within each set of medicament records of the plurality of sets of medicament records, assigning a corresponding relative time being the relative time within the time window, whereby the plurality of sets of medicament records represents the distribution of injections;

for each respective set of medicament records, superimposing the single-shape polygon from each of the medicament records in the respective set of medicament records, wherein the single-shape polygon is superimposed according to the first dimension being the relative time and the second dimension being the amount of injected medicament, wherein an interval along the first dimension is defined by the fixed duration of the time window, and whereby two or more superimposed single-shape polygons may overlap within the interval;

responsive to identifying two or more superimposed overlapping single-shape polygons:
creating a set of multi-shape data structures, comprising a number of multi-shape data structures configured for representing the average and the variability of the distribution of injections, in a displayed mode,
for each multi-shape data structure:
(i) creating a corresponding subset of overlapping single-shape polygons, wherein the subset of overlapping single-shape polygons define a corresponding subset of single-shape data structures,
(ii) calculating a corresponding multi-shape polygon, configured for visualizing a polygon with a two-dimensional shape and according to the first and the second dimension, in the displayed mode, wherein the multi-shape polygon is defined by the overlap between the single-shape polygons of the corresponding subset of overlapping single-shape polygons, which corresponds to the subset of single-shape data structures,
(iii) calculating the number of elements in the subset, being the number of overlapping single-shape data structures in the subset of overlapping single shape polygons,
(iv) calculating a corresponding second intensity indicator, configured for displaying the first visual property of the multi-shape polygon, in the displayed mode, wherein the second intensity indicator is an increasing function of the number of elements in the subset; and communicating display data, wherein the display data comprises:
(i) the plurality of sets of medicament records, and
(ii) the set of multi-shape data structures; and wherein the communication is directed to a display.

In a further aspect is provided a computer-readable data carrier having stored thereon the computer program as described above.

BRIEF DESCRIPTION OF THE DRAWINGS

Like reference numerals refer to corresponding parts throughout the several views of the drawings.

DETAILED DESCRIPTION

The present disclosure relies upon the acquisition of a data set comprising a plurality of blood glucose regulating medicament records taken over a time course. Each respective blood glucose regulating medicament record in the plurality of blood glucose regulating medicament records comprises (i) a respective blood glucose regulating medicament injection event including an amount of blood glucose regulating medicament injected into a subject using a respective injection device in a set of one or more injection devices, and (ii) a corresponding electronic injection event timestamp within the time course that is automatically generated by the respective injection device upon occurrence of the respective blood glucose regulating medicament injection event.

Figure 1:
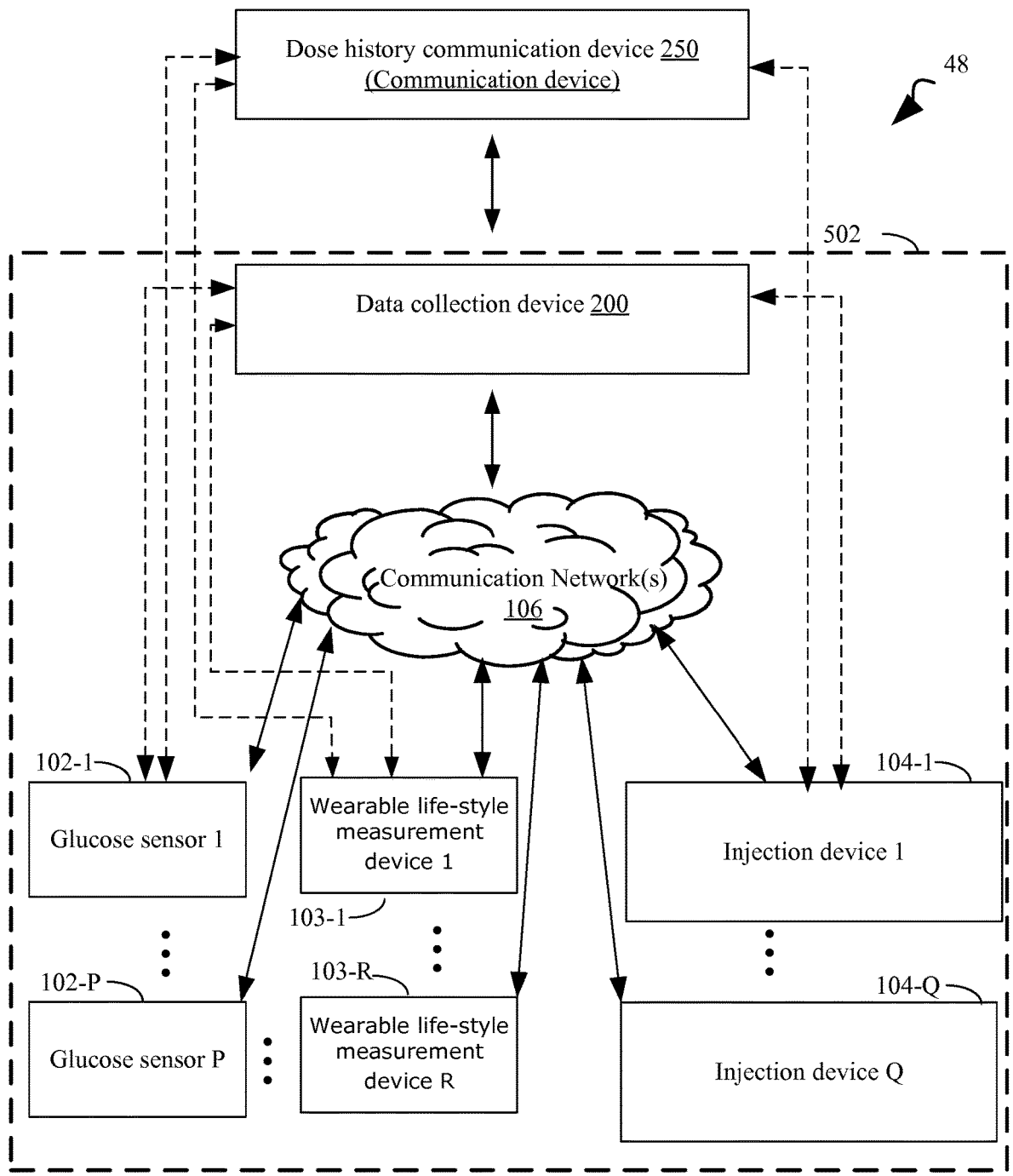
FIG. 1 illustrates an exemplary system topology that includes a dose history communication device for communicating the dose history representing an average and a variability of a distribution of injections with a blood glucose regulating medicament applied by a subject with a treatment regimen, a data collection device for collecting patient data, one or more glucose sensors that measure glucose data from the subject, one or more injection devices that are used by the subject to inject blood glucose regulating medicaments in accordance with the treatment regimen, and one or more wearable life-style measurement devices, where the above-identified components are interconnected, optionally through a communications network, in accordance with an embodiment of the present disclosure.

FIG. 1 illustrates an example of an integrated system 502 for the acquisition of such data. The integrated system 502 includes one or more connected injection devices 104, one or more glucose sensors 102, one or more wearable life-style measurement devices (103), memory (not shown), and a processor (not shown). In some embodiments, a glucose sensor 102 is a continuous glucose monitor. In some embodiments, a continuous glucose monitor will be able to timestamp a life-style event, e.g. meal ingestion or fasting period, which the subject engaged in, and therefore it can for this purpose be regarded as wearable a life-style measurement device.

With the integrated system 502, data from the one or more connected injection devices 104, used to apply a treatment regimen to the subject, is obtained as a plurality of insulin medicament records. Each insulin medicament record comprises a timestamped event specifying an amount of injected blood glucose regulating medicament that the subject received as part of the treatment regimen. The time stamped event specifying the amount of blood glucose regulating medicament is automatically obtained in the sense, that the subject or user of the injection device is not required to perform an active step in order to obtain an electronic or digital time stamp and/or an electronic or digital amount of blood glucose regulating medicament. These data are automatically generated by the injection device upon application of injection, i.e., the injection is applied by the subject or user in order to expel an amount of medicament, but the generation of data is provided irrespective of the users intention, when he or she uses the device. Also, in some embodiments, autonomous timestamped glucose measurements of the subject are obtained. In such embodiments, the autonomous glucose measurements are filtered and stored in non-transitory memory. The plurality of blood glucose regulating medicament records of the subject taken over a time course are used to provide a dose history representing an average and a variability of a distribution of the injections applied by the subject. In this way, the blood glucose medicament records are retrieved and communicated in accordance with the methods of the present disclosure.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein. By the term insulin pen is meant an injection device suitable for applying discrete doses of insulin, where the injection device is adapted for logging and communicating dose related data.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 2:
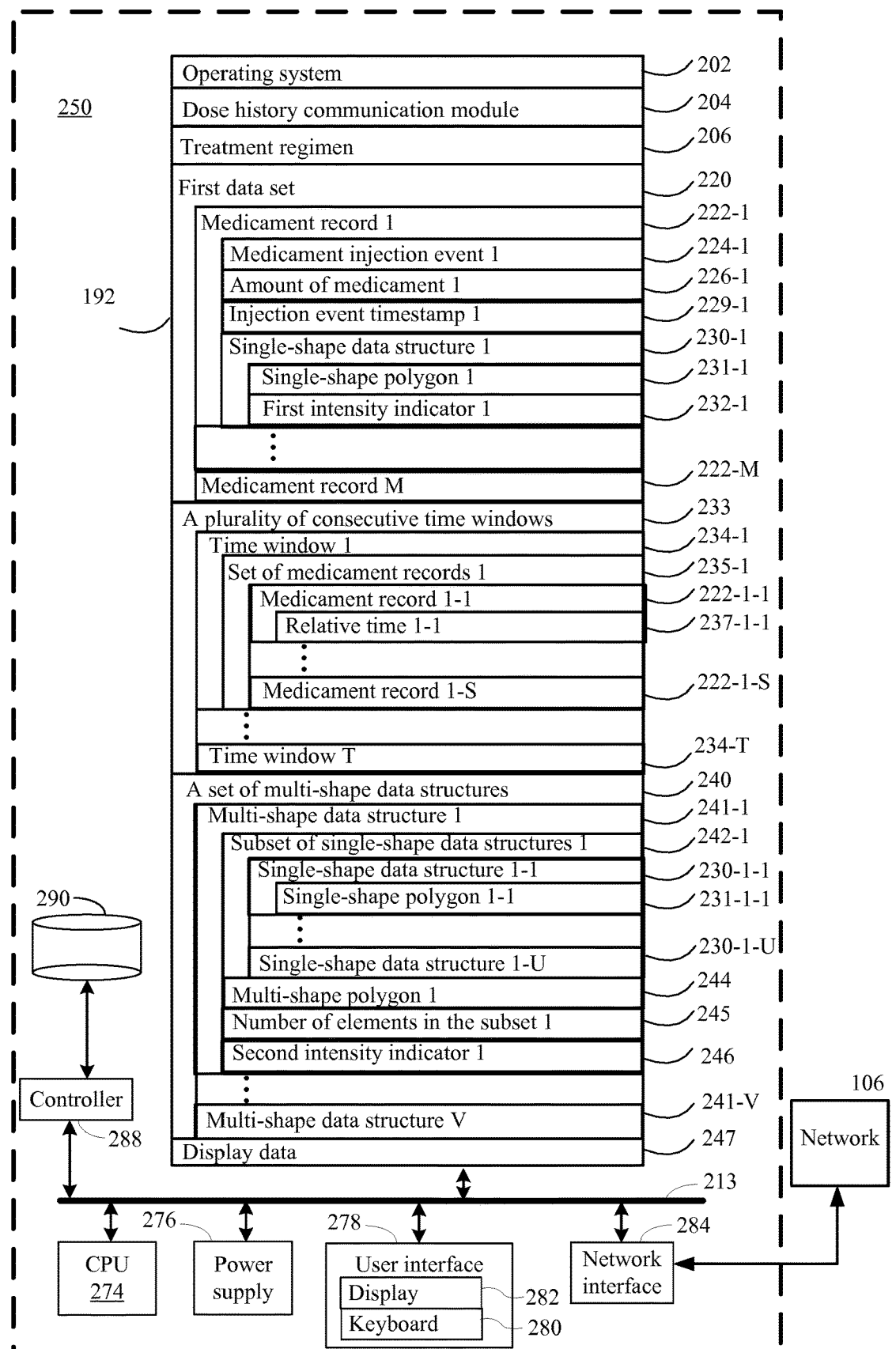
FIG. 2 illustrates a device for communicating a dose history representing an average and a variability of a distribution of injections with a blood glucose regulating medicament applied by a subject with a treatment regimen in accordance with an embodiment of the present disclosure.

A detailed description of a system 48, for communicating a dose history representing an average and a variability of a distribution of injections with a blood glucose regulating medicament in accordance with the present disclosure, is described in conjunction with FIGS. 1 through 3. As such, FIGS. 1 through 3 collectively illustrate the topology of the system in accordance with the present disclosure. In the topology, there is a dose history communication device (250) communicating injections performed by a subject who has applied a treatment regimen (206) within a time course (FIGS. 1, 2, and 3), a device for data collection ("data collection device 200"), one or more injection devices 104 for injecting medicaments into the subject, and optionally one or more glucose sensors 102 associated with the subject. Throughout the present disclosure, the data collection device 200 and the dose history communication device 250 will be referenced as separate devices solely for purposes of clarity. That is, the disclosed functionality of the data collection device 200 and the disclosed functionality of the dose history communication device 250 are contained in separate devices as illustrated in FIG. 1. However, it will be appreciated that, in fact, in some embodiments, the disclosed functionality of the data collection device 200 and the disclosed functionality of the dose history communication device 250 are contained in a single device. In some embodiments, the disclosed functionality of the data collection device 200 and/or the disclosed functionality of the dose history communication device 250 are contained in a single device and this single device is a smart phone.

Figure 3A:
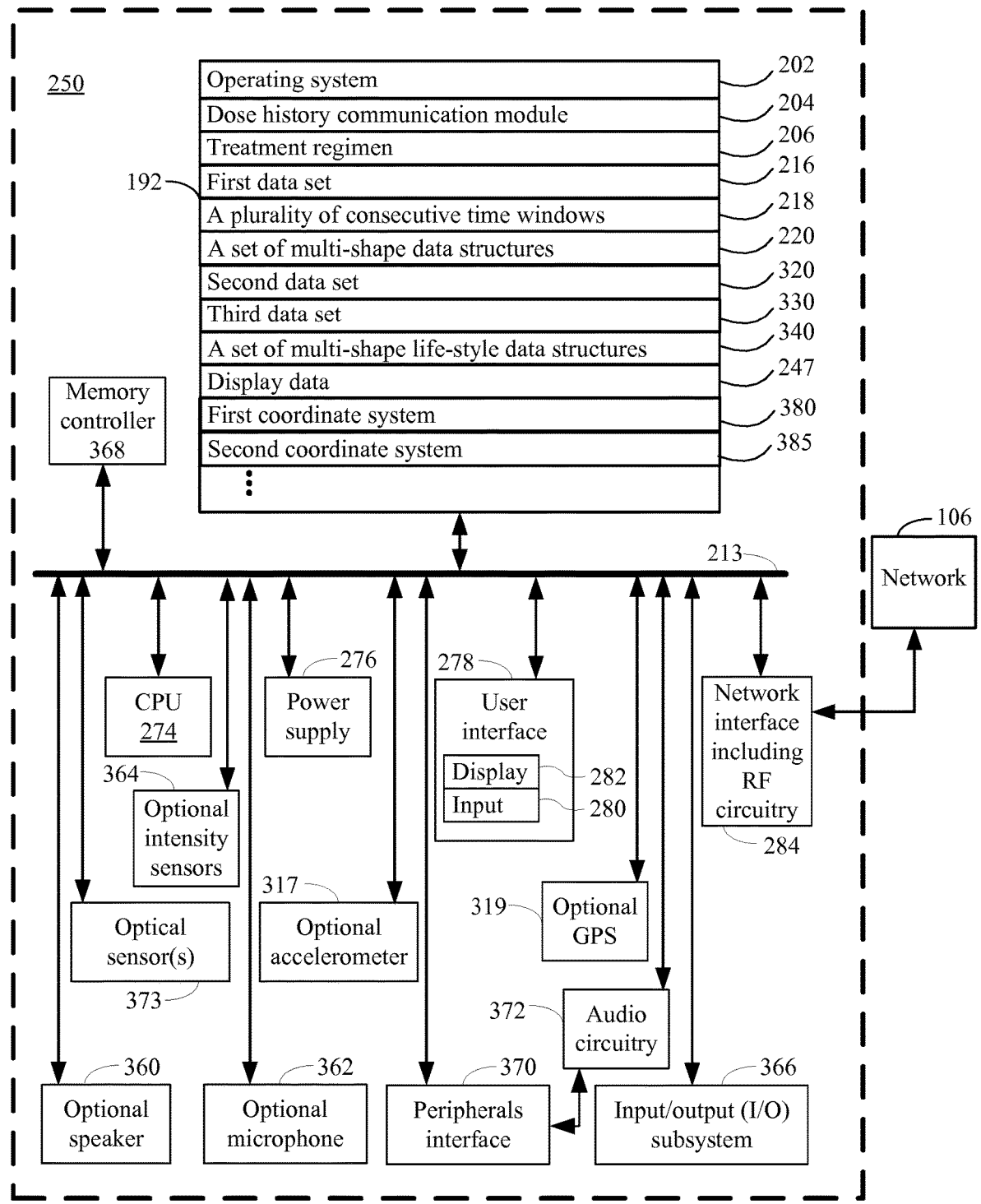
FIGS. 3A, 3B and 3C collectively illustrate a device for communicating a dose history representing an average and a variability of a distribution of injections with a blood glucose regulating medicament applied by a subject with a treatment regimen in accordance with another embodiment of the present disclosure.
Figure 3B:
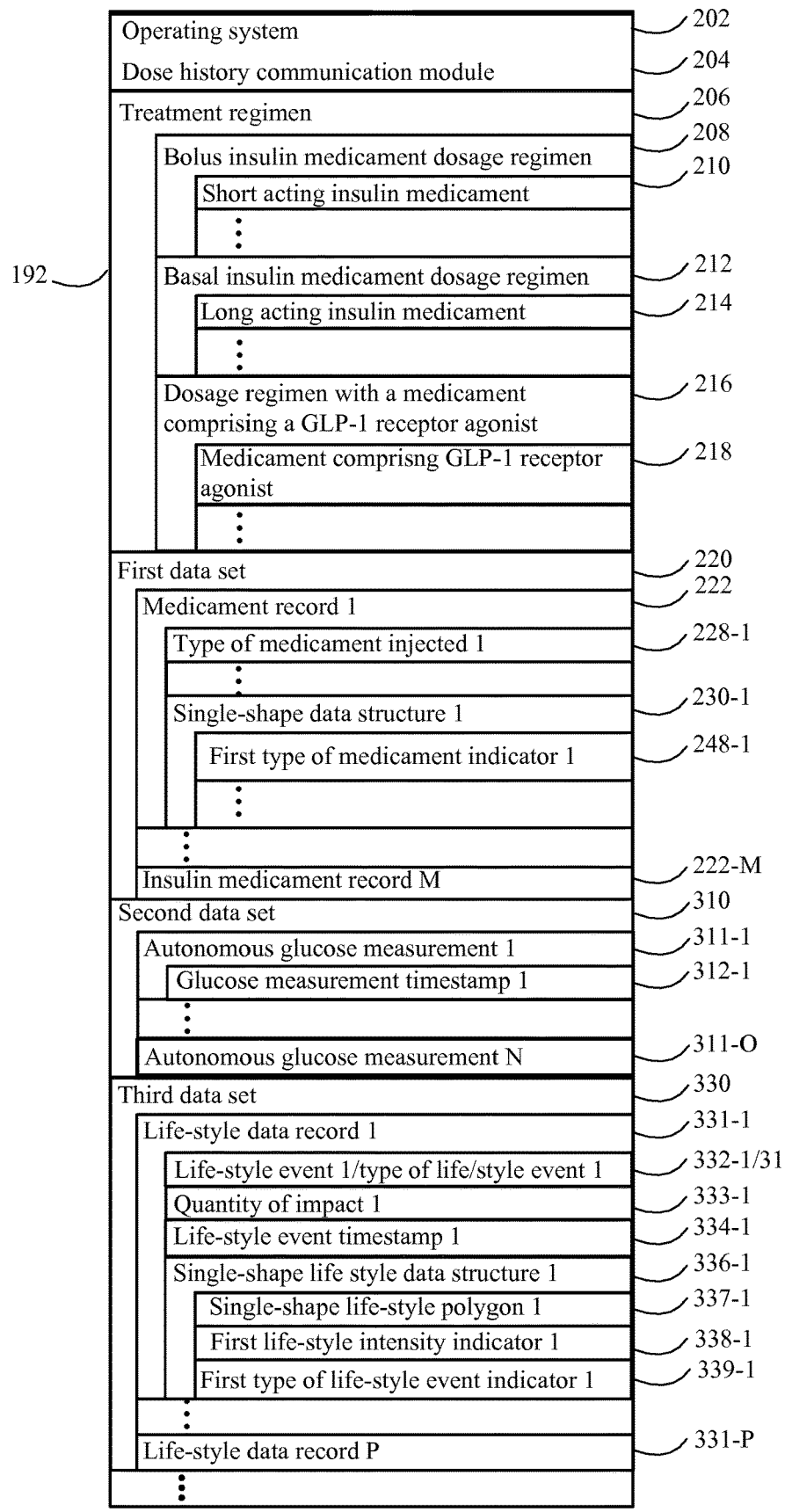

Referring to FIG. 3B, in some embodiments, the treatment regimen (206) comprises a bolus insulin medicament dosage regimen (208) with a short acting insulin medicament (210) or a basal insulin medicament dosage regimen (212) with a long acting insulin medicament (214). In some embodiment the treatment regimen may also comprise a dosage regimen with a medicament comprising a GLP-1 receptor agonist (216) as liraglutide or semaglutide.

Referring to FIG. 1, the dose history communication device 250 communicates a dose history representing an average and a variability of a distribution of injections applied by the subject. To do this, the data collection device 200, which is in electrical communication with the dose history communication device 250, receives a plurality of blood glucose regulating medicament records over a time course, each record comprising (i) a blood glucose regulating medicament injection event including an amount of insulin medicament injected into the subject using a respective injection device 104 in the one or more injection devices, (ii) a respective type of blood glucose regulating medicament (if more than one medicament is applied) injected into the subject from one of short (210) and long acting insulin medicament (214), and alternatively also a medicament comprising a GLP-1 receptor agonist (218), and (iii) a corresponding electronic injection event timestamp that is generated by the respective injection device upon occurrence of the blood glucose regulating medicament injection event. In some embodiments, the data collection device 200 also receives glucose measurements from one or more glucose sensors (e.g., continuous glucose monitors/sensors) 102 used by the subject to measure glucose levels. In some embodiments, the data collection device 200 receives such data directly from the injection devices 104 and/or glucose sensor(s) 102 and/or wearable life-style measurement device (103) used by the subject. For instance, in some embodiments, the data collection device 200 receives this data wirelessly through radio-frequency signals. In some embodiments, such signals are in accordance with an 802.11 (WiFi), Bluetooth, or ZigBee standard. In some embodiments, the data collection device 200 receives such data directly, analyzes the data, and passes the analyzed data to the dose history communication device 250. In some embodiments, an injection device 104, which can be an insulin pen, and/or a glucose sensor 102, and or wearable life-style measurement device (103) includes an RFID tag and communicates to the data collection device 200 and/or the dose history communication device 250 using RFID communication. In some embodiments, the data collection device 200 also receives life-style related event measurements from one or more wearable life-style measurement devices (e.g., meal ingestion sensor measuring a swallowing action, accelerometer measuring exercise etc.) (103) used by the subject to measure the occurrence of a life-style event, the beginning or the ending of such an event and/or to quantify how much the event may affect the blood glucose level of the subject. In some embodiments, the life style measurement device may also generate physiological measurements of the subject (e.g., from wearable physiological measurement devices, or from measurement devices within the data collection device 200 such as a thermometer, etc.).

In some embodiments, the data collection device 200 and/or the dose history communication device 250 is not proximate to the subject and/or does not have wireless capabilities or such wireless capabilities are not used for the purpose of acquiring medicament injection data, autonomous glucose data, and/or life-style related measurement data. In such embodiments, a communication network 106 may be used to communicate insulin medicament injection data from the one or more injection devices 104 to the data collection device 200 and/or the dose history communication device 250, and/or autonomous glucose measurements from the glucose sensor 102 to the data collection device 200 and/or the dose history communication device 250, and/or life-style related event data from one or more life-style measurement devices to the data collection device 200 and/or the dose history communication device 250.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

In some embodiments, the data collection device 200 and/or the dose history communication device 250 is part of an insulin pen. That is, in some embodiments, the data collection device 200 and/or the dose history communication device 250 and an injection device 104 are a single device.

In some embodiments, there is a single glucose sensor 102 attached to the subject and the data collection device 200 and/or the dose history communication device 250 is part of the glucose sensor 102. That is, in some embodiments, the data collection device 200 and/or the dose history communication device 250 and the glucose sensor 102 are a single device.

Of course, other topologies of the system 48 are possible. For instance, rather than relying on a communications network 106, the one or more injection devices 104 and the optional one or more glucose sensors 102 may wirelessly transmit information directly to the data collection device 200 and/or dose history communication device 250. Further, the data collection device 200 and/or the dose history communication device 250 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIG. 2, in typical embodiments, the dose history communication device 250 comprises one or more computers. For purposes of illustration in FIG. 2, the dose history communication device 250 is represented as a single computer that includes all of the functionality for communicating a dose history representing an average and a variability of a distribution of injections applied by the subject. However, the disclosure is not so limited. In some embodiments, the functionality for communicating the dose history is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

Turning to FIG. 2 with the foregoing in mind, an exemplary dose history communication device 250 for communicating a dose history representing an average and a variability of a distribution of injections comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the dose history communication device 250 but that can be electronically accessed by the dose history communication device 250 over an Internet, intranet, or other form of network or electronic cable (illustrated as element 106 in FIG. 2) using network interface 284.

In some embodiments, the memory 192 of the dose history communication device 250 for communicating a dose history representing an average and a variability of a distribution of the injections applied by the subject stores:

an operating system 202 that includes procedures for handling various basic system services;

a medicament duration of action profile for the blood glucose regulating medicament that is characterized by a duration of the blood glucose regulating medicament (not shown on figure);

a dose history communication module 204;

a treatment regimen 206 which the subject is engaged in;

a first data set 220 automatically obtained from one or more injection devices used by the subject to apply the treatment regimen, the first data set comprising a plurality of medicament records over a time course, each respective medicament record 222 in the plurality of medicament records comprising: (i) a respective medicament injection event 224 including an amount of medicament 226 injected into the subject using a respective injection device 104 in the one or more injection devices, (ii) a corresponding electronic injection event timestamp 229 within the time course that is automatically generated by the respective injection device 104 upon occurrence of the respective medicament injection event;

assigned to each of the medicament records 222, a corresponding single-shape data structure 230, configured for representing a single injection in the distribution of injections in a displayed mode, wherein the single-shape data structure 203 comprises: (i) a corresponding single-shape polygon 231, configured for visualizing a two-dimensional shape in the displayed mode, wherein the single-shape polygon is configured to be displayed with: a first length (not shown on FIG. 2) extending in the first dimension, wherein the first length is having a fixed value, or wherein the first length is variable and represents a duration wherein the medicament relating to the respective medicament injection event (224) is still active, and a second length (not shown on FIG. 2) extending in the second dimension, wherein the second length is having a fixed value or is variable and represents the amount of injected medicament 226, or wherein the second length is variable and represents an amount of active medicament remaining from the injected amount of medicament, (ii) a corresponding first intensity indicator 232, configured for displaying a first visual property of the single-shape polygon 231, in the displayed mode;

a plurality of consecutive time windows 233 within the time course, wherein each time window 234 is of the same fixed duration, for each respective time window 234, a set of medicament records 235 comprising a number of medicament records 236, wherein this number can be zero if the set of medicament records 235 is empty.

for each respective medicament record 236 within the respective set of medicament records 235, a corresponding relative time 237 being the relative time within the time window;

a set of multi-shape data structures 240, comprising a number of multi-shape data structures 241 configured for representing the average and the variability of the distribution of the injections;

for each multi-shape data structure 241, (i) a corresponding subset of single-shape data structures 242 having a number of single-shape data structures 243, (ii) a corresponding multi-shape polygon 244, configured for visualizing a two-dimensional shape in the displayed mode, wherein the multi-shape polygon is defined by the overlap between the single-shape polygons of the corresponding subset of overlapping single-shape polygons 542 (illustrated on FIG. 5), (iii) a number of elements in subset 241 being the sum of overlapping single-shape polygons in the subset of single-shape polygons which is the same as the number of elements in the subset of single-shape data structures, (iv) a corresponding second intensity indicator 246, configured for displaying a first visual property of the multi-shape polygon, in the displayed mode, wherein the second intensity indicator 246 is an increasing function of the number of elements in the subset 245;

display data 247 comprising (i) the plurality of sets of medicament records, and (ii) the set of multi-shape data structures 240.

In some embodiments, the dose history communication module 204 is accessible within any browser (phone, tablet, laptop/desktop). In some embodiments the dose history communication module 204 runs on native device frameworks, and is available for download onto the dose history communication device 250 running an operating system 202 such as Android or iOS.

In some implementations, one or more of the above identified data elements or modules of the dose history communication device 250 for communicating a dose event history representing an average and a variability of a distribution of injections are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments, the memory 192 and/or 290 stores additional modules and data structures not described above.

In some embodiments, a dose history communication device 250 for communicating a dose event history representing an average and a variability of a distribution of injections is a smart phone (e.g., an iPHONE), laptop, tablet computer, desktop computer, or other form of electronic device (e.g., a gaming console). In some embodiments, the dose history communication device 250 is not mobile. In some embodiments, the dose history communication device 250 is mobile.

Figure 3C:
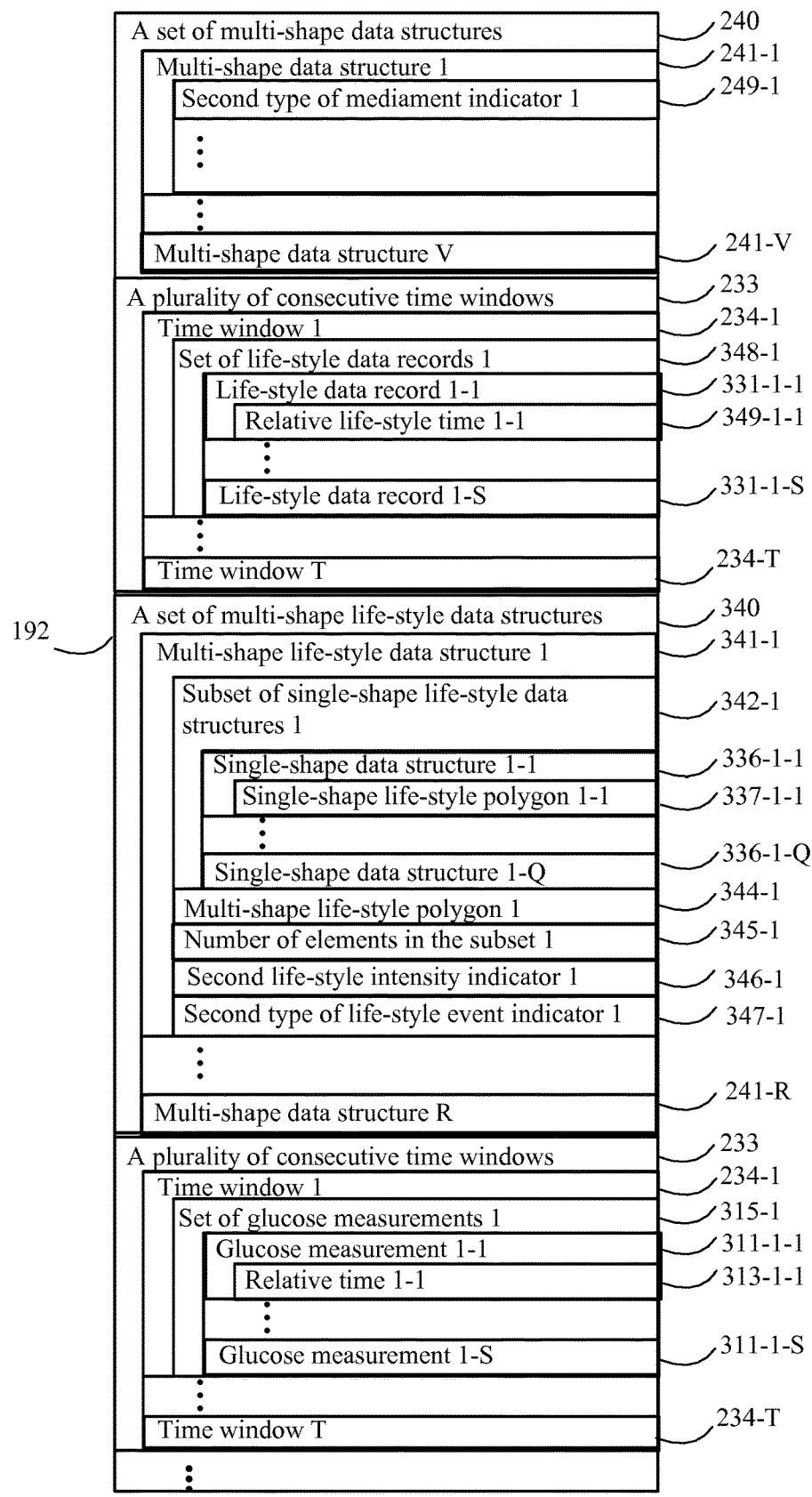

FIGS. 3A, 3B and 3C provides collectively a further description of a specific embodiment of a dose history communication device 250 that can be used with the instant disclosure. The dose history communication device 250 illustrated in FIGS. 3A, 3B and 3C has one or more processing units (CPU's) 274, peripherals interface 370, memory controller 368, a network or other communications interface 284, a memory 192 (e.g., random access memory), a user interface 278, the user interface 278 including a display 282 and input 280 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the dose history communication device 250 (e.g., a touch-sensitive surface such as a touch-sensitive display system 282 of the dose history communication device 250), an optional input/output (I/O) subsystem 366, one or more optional optical sensors 373, one or more communication busses 213 for interconnecting the aforementioned components, and a power supply 276 for powering the aforementioned components.

In some embodiments, the input 280 is a touch-sensitive display, such as a touch-sensitive surface. In some embodiments, the user interface 278 includes one or more soft keyboard embodiments. The soft keyboard embodiments may include standard (QWERTY) and/or non-standard configurations of symbols on the displayed icons.

The dose history communication device 250 illustrated in FIGS. 3A, 3B and 3C optionally includes, in addition to accelerometer(s) 317, a magnetometer (not shown) and a GPS 319 (or GLONASS or other global navigation system) receiver for obtaining information concerning the location and orientation (e.g., portrait or landscape) of the dose history communication device 250 and/or for determining an amount of physical exertion by the subject.

It should be appreciated that the dose history communication device 250 illustrated in FIGS. 3A, 3B and 3C is only one example of a multifunction device that may be used for communicating a dose event history representing an average and a variability of a distribution of injections, and that the dose history communication device 250 optionally has more or fewer components than shown, optionally combines two or more components, or optionally has a different configuration or arrangement of the components. The various components shown in FIG. 3A are implemented in hardware, software, firmware, or a combination thereof, including one or more signal processing and/or application specific integrated circuits.

Memory 192 of the dose history communication device 250 illustrated in FIG. 3A optionally includes high-speed random access memory and optionally also includes non-volatile memory, such as one or more magnetic disk storage devices, flash memory devices, or other non-volatile solid-state memory devices. Access to memory 192 by other components of the dose history communication device 250, such as CPU(s) 274 is, optionally, controlled by the memory controller 368.

The peripherals interface 370 can be used to couple input and output peripherals of the device to CPU(s) 274 and memory 192. The one or more processors 274 run or execute various software programs and/or sets of instructions stored in memory 192, such as the dose history communication module 204, to perform various functions for the dose history communication device 250 and to process data.

In some embodiments, the peripherals interface 370, CPU(s) 274, and memory controller 368 are, optionally, implemented on a single chip. In some other embodiments, they are implemented on separate chips.

RF (radio frequency) circuitry of network interface 284 receives and sends RF signals, also called electromagnetic signals. In some embodiments, the standing treatment regimen 206, the first data set 220, and/or the second data set, and/or the third data set is received using this RF circuitry from one or more devices such as a glucose sensor 102 associated with a subject, an injection device 104 associated with the subject, a the life-style measurement device 103, and/or the data collection device 200. In some embodiments, the RF circuitry 284 converts electrical signals to/from electromagnetic signals and communicates with communications networks and other communications devices, glucose sensors 102, and injection devices 104 and/or the life-style measurement device 200 via the electromagnetic signals. The RF circuitry 284 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 284 optionally communicates with the communication network 106. In some embodiments, the circuitry 284 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the dose history communication device 250. The audio circuitry 372 receives audio data from the peripherals interface 370, converts the audio data to electrical signals, and transmits the electrical signals to the speaker 360. The speaker 360 converts the electrical signals to human-audible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 192 and/or the RF circuitry 284 by the peripherals interface 370.

In some embodiments, the power supply 276 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the dose history communication device 250 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lenses, and converts the light to data representing an image. The optical sensor(s) 373 optionally capture still images and/or video. In some embodiments, an optical sensor is located on the back of the dose history communication device 250, opposite the display 282 on the front of the dose history communication device 250, so that the input 280 is enabled for use as a viewfinder for still and/or video image acquisition. In some embodiments, another optical sensor 373 is located on the front of the dose history communication device 250 so that the subject's image is obtained (e.g., to verify the health or condition of the subject, to determine the physical activity level of the subject, to help diagnose a subject's condition remotely, or to acquire visual physiological measurements of the subject, etc.).

As illustrated in FIG. 3A, a dose history communication device 250 preferably comprises an operating system 202 that includes procedures for handling various basic system services. The operating system 202 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the dose history communication device 250 is a smart phone. In other embodiments, the dose history communication device 250 is not a smart phone but rather is a tablet computer, desktop computer, emergency vehicle computer, or other form or wired or wireless networked device. In some embodiments, the dose history communication device 250 has any or all of the circuitry, hardware components, and software components found in the dose history communication device 250 depicted in FIG. 2 or 3. In the interest of brevity and clarity, only a few of the possible components of the dose history communication device 250 are shown in order to better emphasize the additional software modules that are installed on the dose history communication device 250.

While the system 48 for communicating a dose history representing an average and a variability of a distribution of injections disclosed in FIG. 1 can work standalone, in some embodiments it can also be linked with electronic medical records to exchange information in any way.

As illustrated in FIG. 3A, in some embodiments, the memory 192 of the dose history communication device 250 for communicating a dose history representing an average and a variability of a distribution of the injections applied by the subject further stores one or more of the following data structures: a second data set 320, a third data set 330, a set of multi-shape life-style data structures 340, a first coordinate system 380 and a second coordinate system 385. FIGS. 3B and 3C illustrates further details of the data structures to illustrated in FIGS. 2 and 3A, which can be comprised in some embodiments of the disclosure.

In embodiments where autonomous glucose measurements are used, devices such as the FREESTYLE LIBRE CGM by ABBOTT ("LIBRE") may serve as the glucose sensor 102 in order to make the plurality of autonomous glucose measurements of a subject. The LIBRE allows calibration-free glucose measurements with an on-skin coin-sized sensor, which can send up to eight hours of data to a reader device (e.g., the data collection device 200 and/or the dose history communication device 250) via near field communications, when brought close together. The LIBRE can be worn for fourteen days in all daily life activities. In some embodiments, the autonomous glucose measurements are autonomously taken from the subject at an interval rate of 5 minutes or less, 3 minutes or less, or 1 minute or less. In some embodiments, the autonomous glucose measurements are taken from the subject at an interval rate of 5 minutes or less, 3 minutes or less, or 1 minute or less, over a time period of a day or more, two days or more, a week or more, or two weeks or more. In some embodiments, the autonomous glucose measurements are autonomously taken (e.g., without human effort, without human intervention, etc.).

Figure 4:
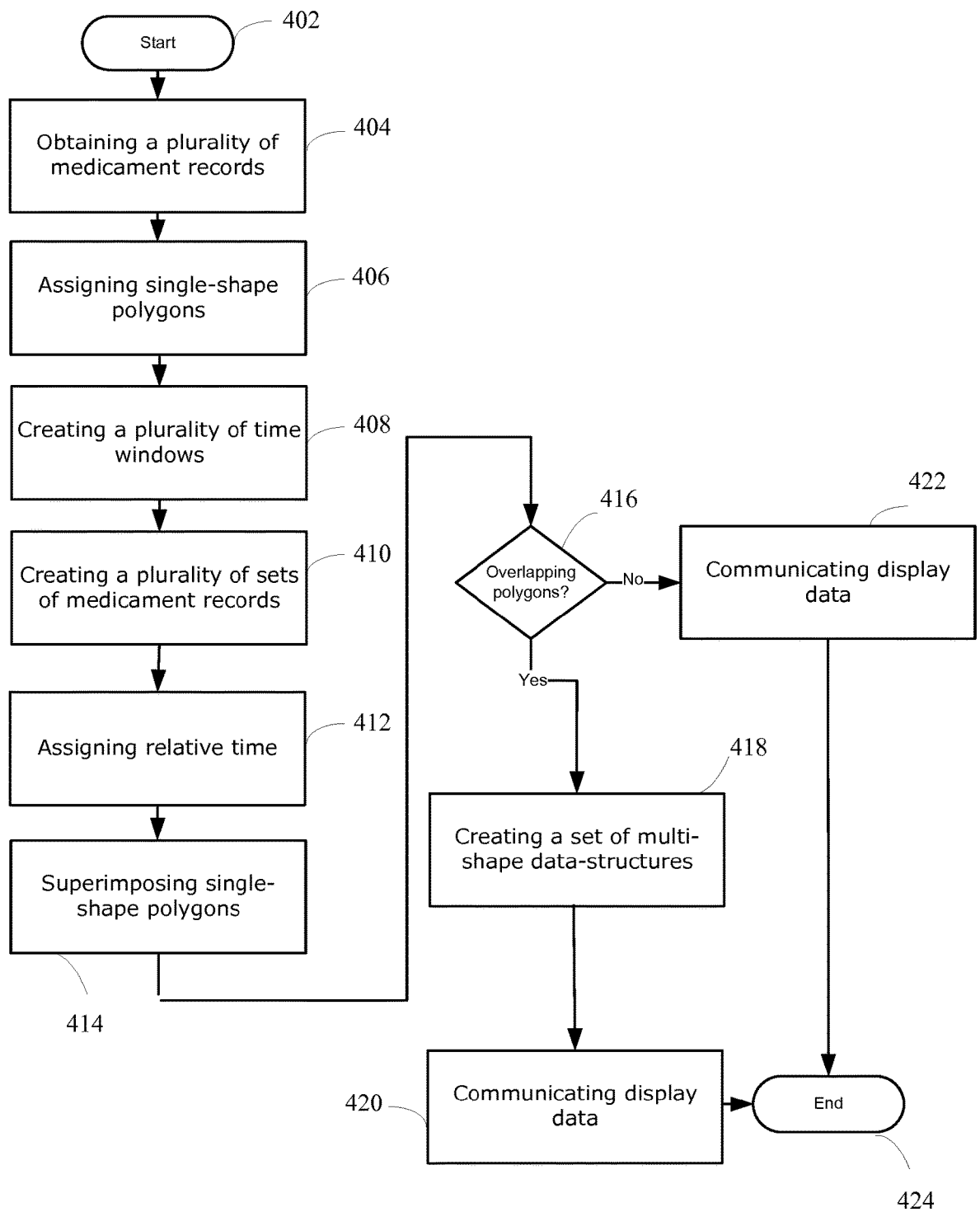
FIG. 4 provide a flow chart of processes and features of a device for communicating a dose history representing an average and a variability of a distribution of injections with a blood glucose regulating medicament applied by a subject with a treatment regimen, in accordance with various embodiments of the present disclosure.

Now that details of a system 48 for communicating a dose event history representing an average and a variability of a distribution of injections have been disclosed, details regarding a flow chart of processes and features of the system, in accordance with an embodiment of the present disclosure, are disclosed with reference to FIG. 4. In some embodiments, such processes and features of the system are carried out by the insulin dose history communication module 204 illustrated in FIGS. 2 and 3.

Blocks 402-424. With reference to FIG. 4, the goal of insulin therapy in subjects with either type 1 diabetes mellitus or type 2 diabetes mellitus is to match as closely as possible normal physiologic insulin secretion to control fasting and postprandial plasma glucose, and data collection and presentation is an important component in order to understand the progress in the treatment. As illustrated in FIG. 2, a device 250 is provided for communicating a dose history configured for representing an average and a variability of a distribution of injections with a blood glucose regulating medicament applied by a subject with a treatment regimen. The device comprises one or more processors 274 and a memory 192/290, the memory storing instructions that, when executed by the one or more processors, performs a method which will be described below and illustrated in FIG. 4. By configuring the processor, the memory and the stored instructions, as described above, the dose history communication device 250 is configured or adapted to perform the method.

Referring to FIG. 4, the block 402 indicates a starting point of the method, and block 404 represent a step of obtaining a first data set 220 from one or more injection devices 104 used by the subject to apply the treatment regimen 206. The first data set 220 comprises a plurality of medicament records taken over a time course, each respective medicament record 222 in the plurality of medicament records comprises: (i) a respective medicament injection event 224 including an amount of medicament 226 injected into the subject using a respective injection device 104 in the one or more injection devices, (ii) a corresponding electronic injection event timestamp 229 within the time course that is automatically generated by the respective injection device upon occurrence of the respective medicament injection event 224.

Figure 6A:
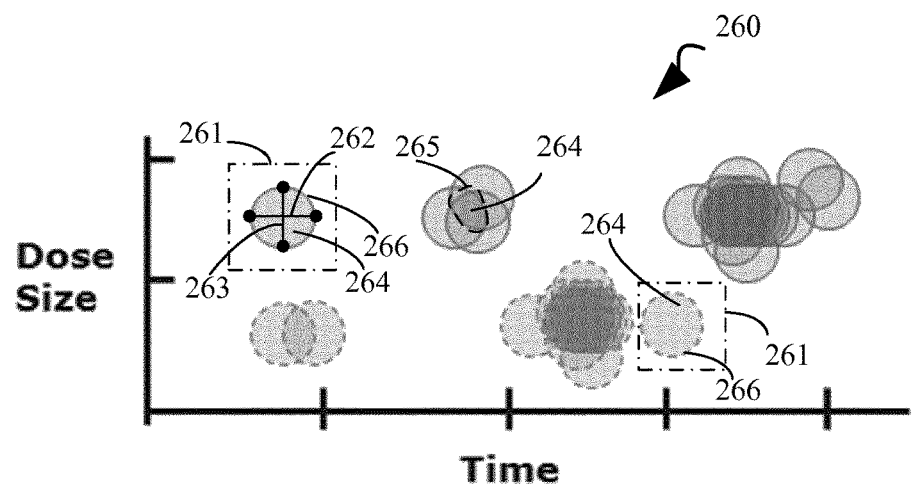
FIGS. 6A and 6B collectively illustrates various features of the data structures in a displayed mode, in accordance with an embodiment of the present disclosure.
Figure 6B:
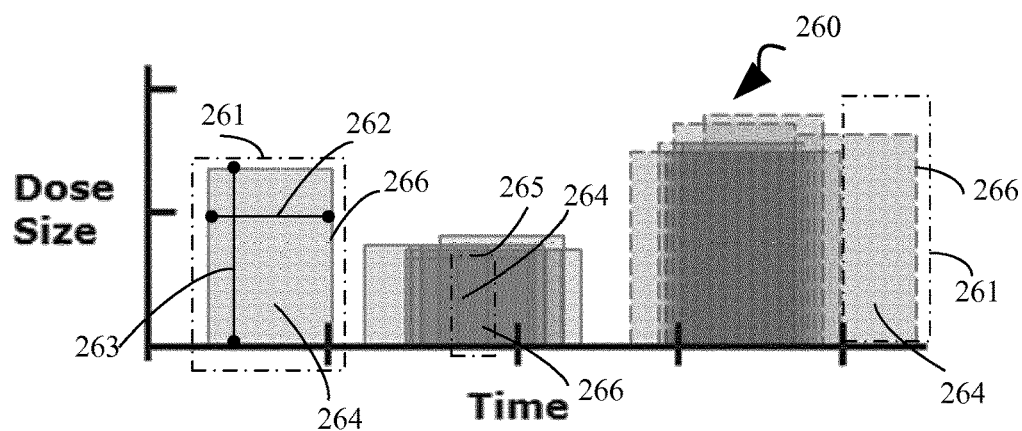

Block 406 represents another step in the method, wherein each of the medicament records 222 are assigned a corresponding single-shape data structure 230. The single-shape data structure 230 is configured for representing a single injection in the distribution of injections in a displayed mode 260, and the graphical displayed mode is illustrated in FIG. 6. The single-shape data structure 230 comprises (i) a corresponding single-shape polygon 231, configured for visualizing a polygon 261 with a two-dimensional shape, in the displayed mode. As illustrated in FIGS. 6A and 6B, the single-shape polygon 231 is configured to be displayed with a first length 262 extending in the first dimension, wherein the first length 262 is having a fixed value, and a second length 263 extending in the second dimension, wherein the second length 263 is having a fixed value (FIG. 6A) or is variable and represents an amount of injected medicament (FIG. 6B). The single-shape data structure 230 further comprises (ii) a corresponding first intensity indicator 232, configured for displaying a first visual property 264 of the single-shape polygon 261, in the displayed mode 260.

FIG. 6, also illustrates that the single-shape polygon 231, can be visualized as a polygon 261 being in the form of a circle (FIG. 6A) and in the form of a rectangle (FIG. 6B). The first visual property 264 is illustrated as a transparency and the intensity can be defined by the corresponding first intensity indicator 232. The first visual property could also be a temperature map, where the intensity indicator 232 would define the intensity. For a low intensity the colour could be blue and for a high intensity the colour could be red.

Figure 5:
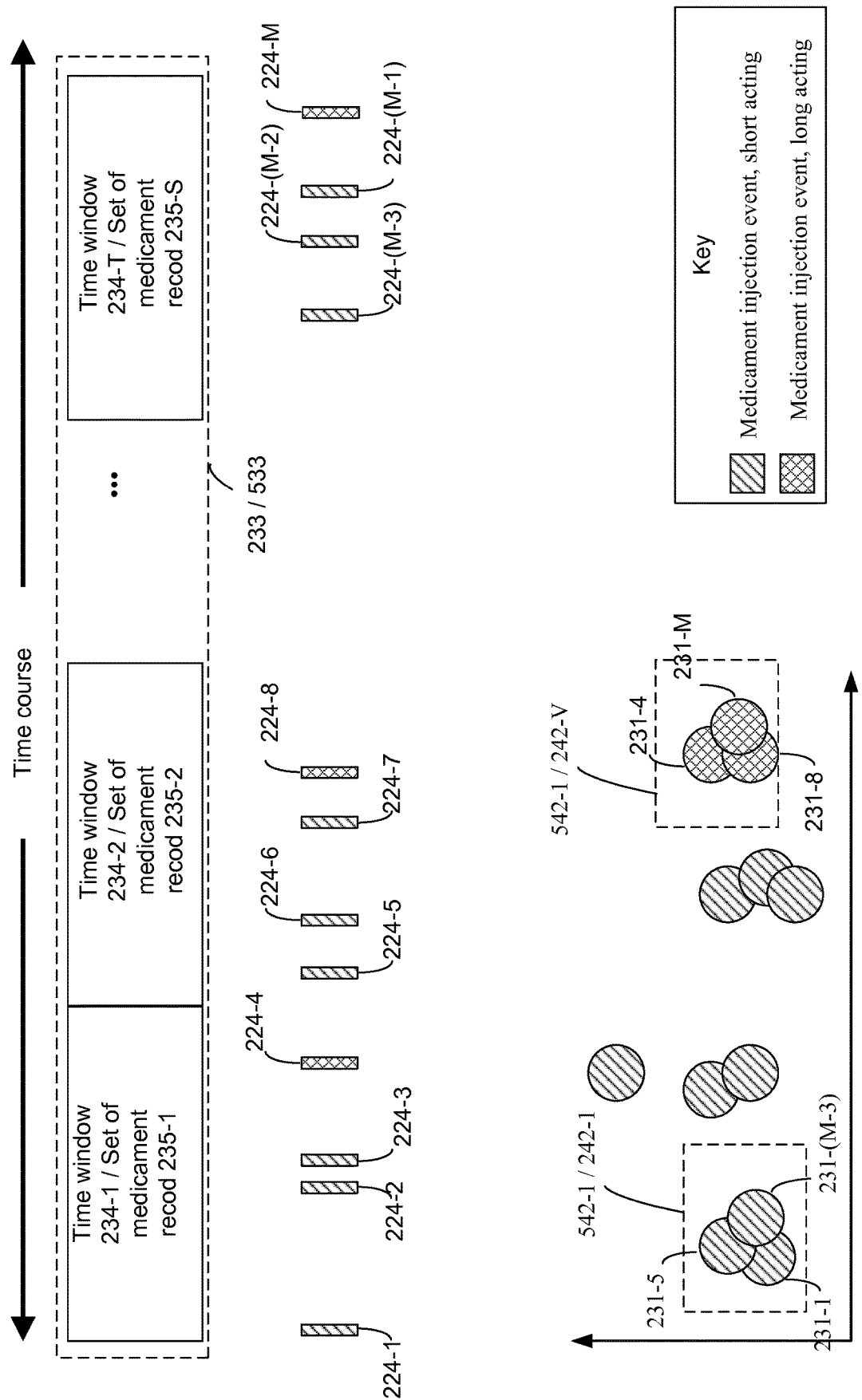
FIG. 5 illustrates a step of creating a plurality of time windows, a step of creating a plurality of sets of medicament records, and a step of superimposing single-shape polygons, in accordance with an embodiment of the present disclosure.

Block 408 represents another step of the method, wherein the step comprises creating a plurality of consecutive time windows 233 within the time course, wherein each time window 234 is of the same fixed duration, as illustrated on the upper part of FIG. 5.

For each respective time window 234, another step, represented by block 410, comprises creating a set of medicament records 235, and thereby implicitly creating a plurality of sets of medicament records 533 (upper part of FIG. 5). In this way, each respective set of medicament records 235 in the plurality of medicament records 533, comprises a number of medicament records from the first data set 220, and each respective medicament record 222 within the respective set of medicament records 235 have a timestamp 229 in the respective time window 234.

Block 412 represents another step of the method. For each respective medicament record 222, within each set of medicament records 235 of the plurality of sets of medicament records 533, the step comprises assigning a corresponding relative time 237 to the respective medicament record 222. For this purpose, the relative time is defined as the relative time within the window 234, e.g., measured as the time from the beginning of the time window to the point in time in the time window indicating the incidence of the injection event. The incidence of the injection in the time window is identified by the time stamp. In this way, the plurality of sets of medicament records 533 represents the distribution of injections.

Block 414 represents another step of the method. For each respective set of medicament records 235, the step comprises superimposing the single-shape polygon 231 from each of the medicament records 224 in the respective set of medicament records 235. The single-shape polygon 231 is superimposed according to the first and the second dimension, as shown in the lower part of FIG. 5. An interval along the first dimension is defined by the fixed duration of the time window, and as a consequence of the polygons being superimposed, two or more superimposed single-shape polygons 231 may overlap within the interval. On FIG. 5, the length in the first dimension for the time window 234 and the length of the interval are not drawn in scale. Also, the relative position of each medicament injection event 224 in the time window in the upper part of FIG. 5, does not drawn to correspond exactly to its relative position in the coordinate system illustrating the superimposition step in the lower part of FIG. 5.

Block 416 illustrates a conditioned response in the process, and responsive to identifying two or more superimposed overlapping single-shape polygons 231, after the superimposition step, the method proceeds to the step illustrated by block 418. If none of the polygons are overlapping the method may proceeds to the step illustrated by block 422.

Block 418 represents another step of the method, the step comprises creating a set of multi-shape data structures 240, comprising a number of multi-shape data structures 241 configured for representing the average and the variability of the distribution of injections, in a displayed mode 260, as illustrated in FIG. 6. For each multi-shape data structure 241, the step comprises (i) creating a corresponding subset of overlapping single-shape polygons 542, wherein the subset of overlapping single-shape polygons 542 define a corresponding subset of single-shape data structures 242, as also illustrated on FIG. 6 by framing a subset of overlapping single-shape polygons 542-1, and by also indicating that they belong to the subset of single-shape data structures 242-1.

FIG. 6 also illustrates that the first multi-shape data structure 241-1 within the set of multi-shape data structures 240, comprises the subset of single-shape data structures 242-1 defined or identified by the subset of single-shape polygons 542-1. The individual elements in the subset of single-shape polygons 542-1 is, in the illustrated example, single-shape polygon 231-1, a single-shape polygon 231-5, and single-shape polygon 231-(M-3).

The single-shape polygons 231-1, 231-5, 231-(M-3) have corresponding medicament injection events 224-1, 224-5, 224-(M-3) illustrated in the upper part of FIG. 5. Each of the medicament injection events 224-1, 224-5, 224-(M-3) belong to different time windows. Even though the data structures indicating the plurality of medicament records 533 and the subset of single-shape polygons 542 are not shown on FIG. 2-3, they can also be stored in the memory 192 of the dose history and communication device 250.

The step illustrated by block 418 further comprises (ii) calculating a corresponding multi-shape polygon 244, configured for visualizing a polygon 265 with a two-dimensional shape, in the displayed mode 260, as illustrated in FIG. 6. The polygon visualized by the multi-shape polygons 244 of different multi-shape data structures can be different, as the multi-shape polygon 244 is defined by the overlap between the single-shape polygons 231 of the corresponding subset of overlapping single-shape polygons, which corresponds to the subset of single-shape data structures 242. The step further comprises (iii) calculating the number of elements in the subset 245, being the number of overlapping single-shape data structures 230 in the subset of overlapping single shape polygons 242. The step further comprises, (iv) calculating a corresponding second intensity indicator 246, configured for displaying the first visual property 264 of the multi-shape polygon 231, in the displayed mode, wherein the second intensity indicator 246 is an increasing function of the number of elements in the subset 245.

Block 420 represents another step of the method, the step comprising communicating display data 247, wherein the display data 247 comprises (i) the plurality of sets of medicament records 533, and (ii) the set of multi-shape data structures 240. The communication is directed to (i) the subject or (ii) to a health care provider, and the communication is for providing the dose history representing the average and the variability of the distribution of the injections. Alternatively the communication could be directed to a person related to the subject.

Figure 7:
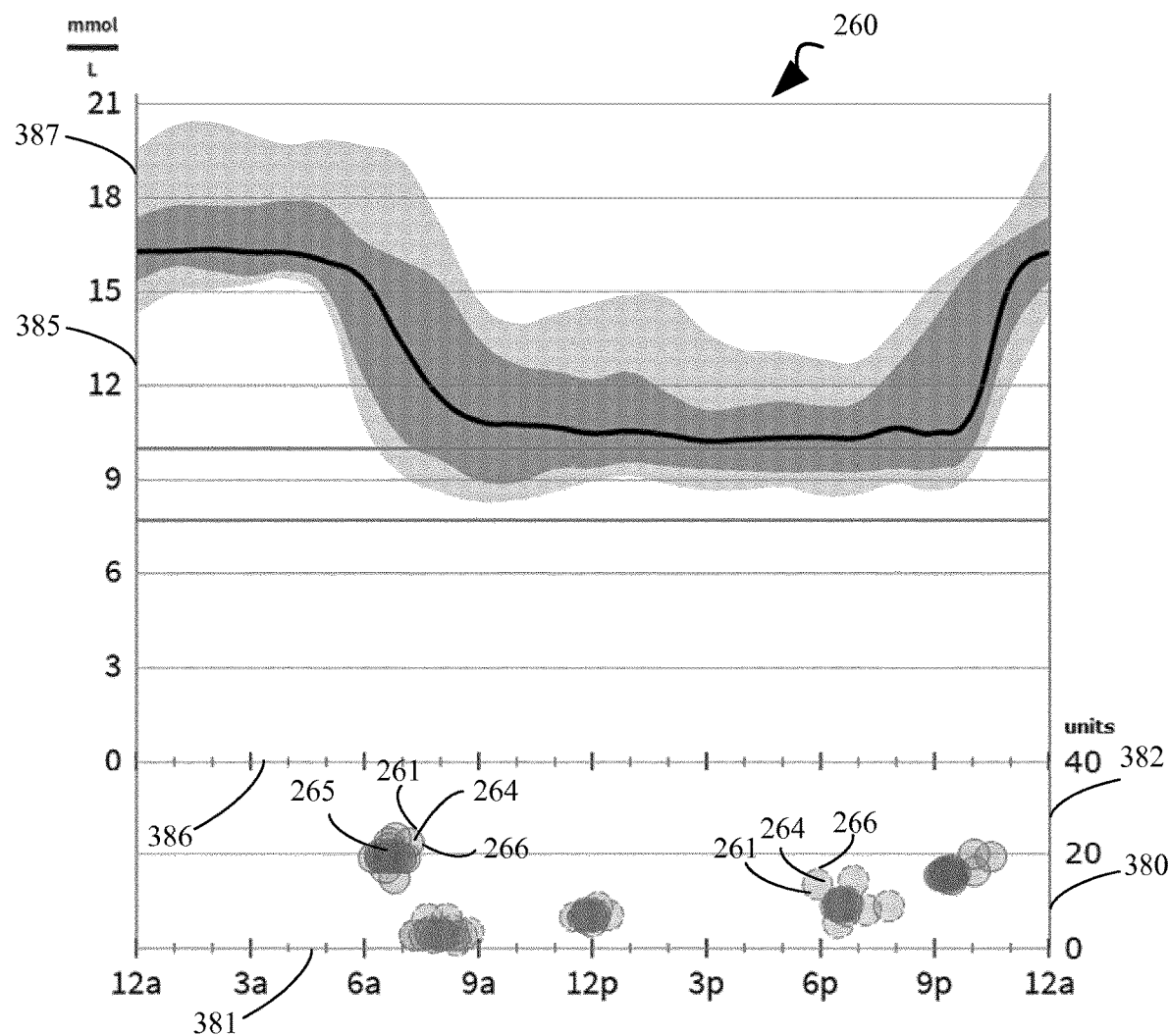
FIG. 7 illustrates a displayed dose history representing an average and a variation of a distribution of injection events (lower coordinate system), and an average and a variation of a distribution a blood glucose measurement events, in accordance with an embodiment of the present disclosure.
Figure 8:
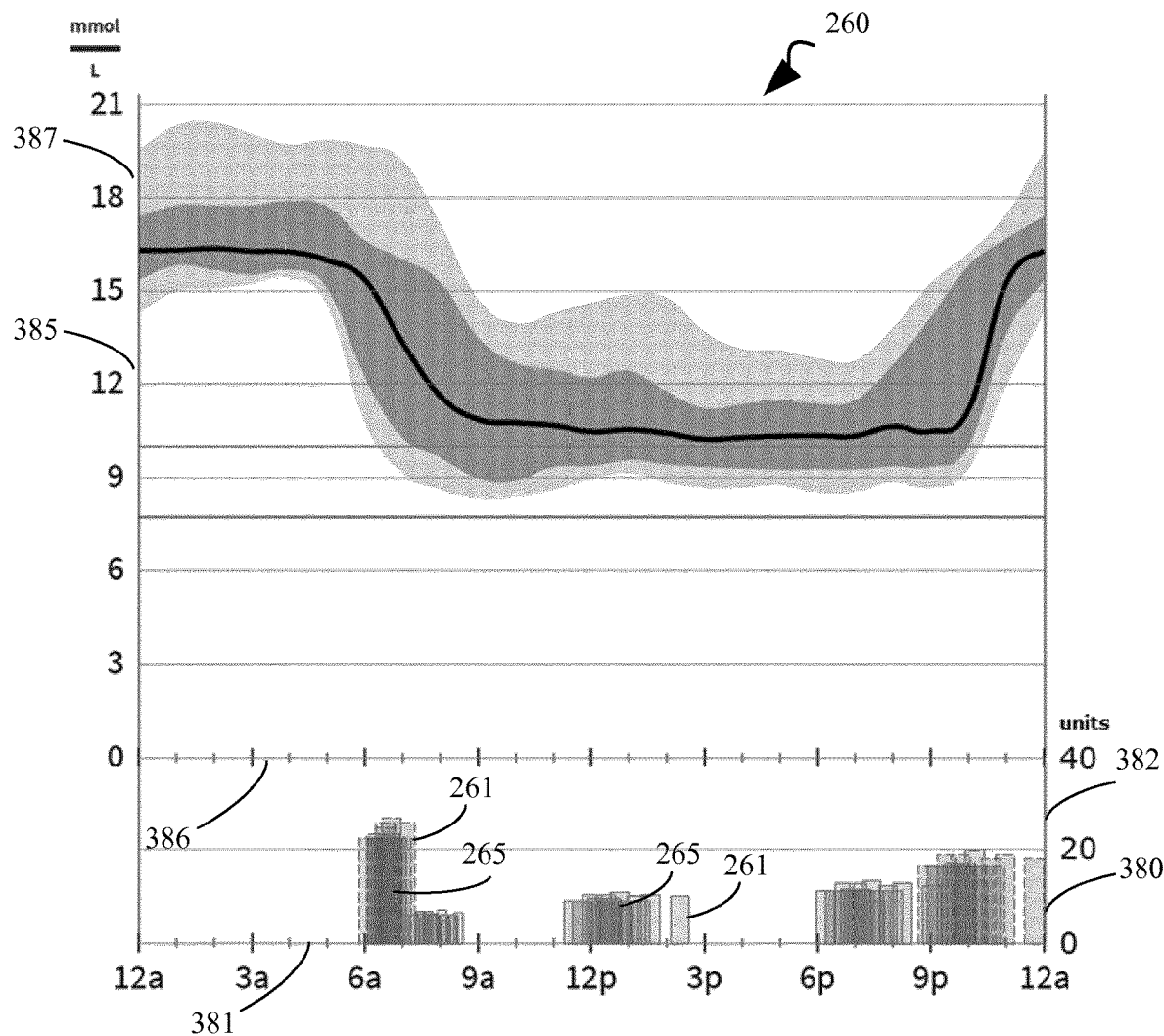
FIG. 8 illustrates a displayed dose history representing an average and a variation of a distribution of injection events (lower coordinate system), and an average and a variation of a distribution a blood glucose measurement events, in accordance with another embodiment of the present disclosure.

The lower panel or coordinate system of FIGS. 7-8 illustrates communicated dose histories representing the average and the variability of the distribution of the injections. In FIG. 7, the injections are indicated by polygons in the form of a circle, and the position of the circle indicates the relative time, and the amount of injected medicament. I FIG. 8, the injections are indicated by polygons in the form of a bar, and the position of the bar in the first dimension indicates the relative time, and the height of the par indicates, in the second dimension, the amount of injected medicament. FIGS. 7-8 will be discussed in further details later.

In some embodiments, as illustrated on FIG. 3B, the treatment regimen comprises a bolus insulin medicament dosage regimen 208 with a short acting insulin medicament 210 and a basal insulin medicament dosage regimen 212 with a long acting insulin medicament 214. Although, the embodiment illustrated in FIG. 3B comprises three dosage regimen, embodiments only comprising one dosage regimen is also possible according to the present disclosure, i.e., the treatment regimen may comprise a bolus insulin medicament dosage regimen 208 with a short acting insulin medicament 210 or a basal insulin medicament dosage regimen 212 with a long acting insulin medicament 214 or a dosage regimen with a medicament comprising a GLP-1 receptor agonist (216) comprising a medicament comprising a GLP-1 receptor agonist (218) or any combination of the listed dosage regimens. In general the dosage regimen could comprise any medicament being a blood glucose regulating medicament, where it would be desirable to view the distribution of injections, and get an impression of the average and the variation of the distribution, in order to obtain insight of how the treatment progresses and how the medicament is administrated.

In some embodiments, the dose history communication device 250 further comprises a display 282, as illustrated on FIGS. 2 and 3, and wherein the step of communicating display data 247 further comprises displaying the display data 247 in a first coordinate system 380, as illustrated on FIGS. 7 and 8, on the display 282. As further illustrated in FIGS. 7 and 8, a first coordinate axis 381 is defined by the first dimension, and the second coordinate axis 382 is defined by the second dimension. The step further comprises displaying each respective medicament record 222, in each respective set of medicament records 235, in each of the plurality of sets of medicament records 533, by arranging the corresponding single-shape polygon 231 in the first coordinate system 380 according to the corresponding relative time 237 and the corresponding amount of medicament 226, and wherein the visual property 264 of the single-shape polygon has been defined by the corresponding first intensity indicator 232. The single shape-polygon 231 is visualized by the two-dimensional polygon 261 in FIGS. 7 and 8. The step further comprises displaying each respective multi-shape data structure 241, in the set of multi-shape data structures 240, by arranging the corresponding multi-shape polygon 244 in the first coordinate system 380, according to a position defined by the subset of overlapping single-shape polygons 542, and wherein the first visual property 264 of the multi-shape polygon 244 has been defined by the corresponding second intensity indicator 246. The multi shape-polygon 244 is visualized by the two-dimensional polygon 265 in the displayed mode 260 illustrated in FIGS. 7 and 8.

In some embodiments, each respective medicament record 222 in the plurality of medicament records further comprises 533 a corresponding type of medicament 228 injected into the subject. In order to represent the data structure in the displayed mode, the single-shape data structure 232 corresponding to the respective medicament record 222 further comprises a corresponding type of medicament indicator 248, configured for displaying a second visual property 266 of the single-shape polygon 231, and thereby indicating the type of medicament 228 injected into the subject.

In order to be able to represent a multi-shape polygon defined by a homogeneous group of single-shape polygons, each of the single-shape data structures 230 within the corresponding subset of single-shape data structures 242 are having the same type of medicament indicator 248, thereby indicating that they relate to injections with the same type of medicament 228. Similarly to the single-shape data structure, each multi-shape data structure 241 within the set of multi-shape data structures 240 further comprises a second type of medicament indicator 249 defined by the type of medicament indicator 248 of the corresponding subset of single-shape data structures. Again, the second type of medicament indicator, is configured for displaying the second visual property 266 of the multi-shape polygon, and thereby indicating the type of medicament 228 injected into the subject, whereby the set of multi-shape data structures 240 is further configured for representing distributions relating to injections with different types of medicament.

In FIGS. 6-8 the first visual property 264 of the two dimensional polygons 261 representing the single-shape polygon 231 and 265 representing the multi-shape polygon 244, is illustrated by a transparent grey. In this case, at relatively low values of the first 232 or second 246 intensity indicator the first visual property 264 is grey with a high transparency, and at relatively high values of the first 232 or second 246 intensity indicator, the first visual property 264 is grey with a low transparency. In other embodiments the first visual indicator may be defined by a grayscale. In this case, at relatively low values of the first or second intensity indicator the first visual property 264 is light grey, and at relatively high values of the first or second intensity indicator, the first visual property 264 is dark grey or black. In some embodiments another colourscale may be used, e.g., different shades of red, blue, green etc. In some embodiments the colourscale could be defined by a temperature scale, where blue is defined for relatively low values of the first or second intensity indicator, and wherein the first visual indicator turns into a more red colour at higher values for the first 232 or second 246 intensity indicator. In some embodiments the first visual property 264, may be a combination of a colour and a transparency scale.

In FIGS. 6-8 the second visual property 266 of the two dimensional polygons 261 representing the single-shape polygon 231 and 265 representing the multi-shape polygon 244, is illustrated by different borders of the polygon, i.e., the border lines are either dashed or solid. For one type of medicament injected, the corresponding first type of medicament indicator 248 and the second type of medicament indicator 249 may specify that the second visual property should be a dashed border line, and for another type of medicament the medicament indicators 248, 249 specify that the second visual property should be a solid border line. In other embodiments the second visual indicator may be a colour, wherein the medicament indicators 248, 249 for one type of medicament injected 228 (e.g. a short acting insulin) specifies that the second visual property 266 should be displayed as green, wherein the medicament indicators 248, 249 for another type of medicament injected 228 (e.g. a long acting insulin) specified that the second visual property 266 should be displayed as red. Of course other types of colours and lines could be implemented in other embodiments.

In some embodiments, the dose history communication device 250 further comprises a display 282, as illustrated on FIGS. 2 and 3, and the step of communicating display data further comprises displaying the display data 247 in a first coordinate system 380 on the display 288, wherein a first coordinate axis 381 is defined by the first dimension, and the second coordinate axis 382 is defined by the second dimension. The step further comprises displaying each respective medicament record 222, in each respective set of medicament records 235, in the plurality of sets of medicament records 533, by arranging each of the single-shape polygons 231 corresponding to the respective medicament record 222 in the coordinate system 380 according to the corresponding relative time 237 and the corresponding amount of medicament 226, and wherein the first visual appearance has been defined by the first intensity indicator 232 and the second visual appearance has been defined by the first type of medicament indicator 248, wherein both indicators are corresponding to the respective medicament record 222. The step further comprises displaying each respective multi-shape data structure 241, in the set of multi-shape data structures 240, by arranging each of the multi-shape polygons 244 corresponding to the respective multi-shape data structure 241 in the coordinate system 380, according to a position defined by the subset of overlapping single-shape polygons 542, and wherein the first visual appearance 264 has been defined by the second intensity indicator 246 and the second visual appearance 266 has been defined by the second type of medicament indicator 249.

In some embodiments, the display 288 further comprises a second coordinate system 385 comprising a first axis 386 and a second axis 387, as illustrated on FIGS. 7-8, and wherein the second coordinate system represents an average and a variability of a distribution based on glucose data obtained within the time course. For the first coordinate system 380, the second axis 382 represents the amount of injected medicament 226, and for the second coordinate system 385, the second axis 387 represents a blood glucose concentration. The first axis 381, 386 of both coordinate systems 380, 385 represent the time and are defined within the interval defined by the time window 234. The first axis 381, 386 of both coordinate systems 380, 385 have been arranged in parallel on top of each other or with an off-set in the direction of the second axis 382, 387, and the second axis 382, 387 of both coordinate systems 380, 385 have been arranged in parallel.

In some embodiments, the single-shape polygon 231 is configured for visualizing a polygon 261 with a two-dimensional shape defining a circle, and wherein the second length 263 is having a fixed value.

In some embodiments, the method further comprises obtaining a second data set 310, wherein the second data set 310 comprises a plurality of autonomous glucose measurements of the subject within the time course and, for each respective autonomous glucose measurement 311 in the plurality of autonomous glucose measurements, a glucose measurement timestamp 312 representing when the respective measurement was made. The step further comprises, for each respective time window 234, creating a set of glucose measurements 315, and thereby creating a plurality of sets of glucose measurements, and wherein each glucose measurement 311 within the respective set of glucose measurements 315 have a timestamp 312 in the respective time window. The method further comprises, for each respective glucose measurement 311, a step associating a corresponding relative time 313 being the relative time within the time window, whereby the plurality of sets of glucose measurements are representing a distribution of glucose measurements within the time window. The method further comprises the step of calculating, for the plurality of sets of glucose measurements, the average and the variability as a function of the relative time. Therefore, the display data further comprises the plurality of sets of glucose measurements, the corresponding relative time, and the calculated average and the variability as a function of the relative time.

In some embodiments, the dose history communication device 250 is further adapted for communicating a life-style event history representing an average and a variability of a distribution of life-style related events within the time course, which the subject has engaged in. In analogy with the method of representing injection events, the method further comprises obtaining a third data set 330 from one or more wearable life-style measurement devices 103 used by the subject to acquire life-style data, the third data set 330 comprises a plurality of life-style data records 331 over the time course, each respective life-style data record 331 in the plurality of life-style data records comprises: (i) a respective life-style event 332, (ii) a corresponding electronic life-style event timestamp 334 within the time course that is automatically generated by the respective life-style measurement device 103 upon occurrence of the respective life-style related event, or by user actuation of the respective life-style measurement device, or a begin timestamp and an end timestamp indicating the beginning and the ending time of the life-style event engaged in by the subject. Each of the life-style data records 331 are assigned a corresponding single-shape life-style data structure 336, configured for representing a single event in the distribution of life-style related events. The single-shape life-style data structure 336 comprises: (i) a corresponding single-shape life-style polygon 337, configured for visualizing a polygon with a two-dimensional shape in the displayed mode, wherein the single-shape life-style polygon 337 is configured to be displayed with a first length extending in the first dimension. The first length is having a fixed value, or is representing a duration of the life-style event the subject engaged in, based on a response to an indication of that a begin time stamp and an end timestamp has been recorded. The single-shape life-style polygon 337 is further configured to be displayed with a second length extending in the second dimension. The single-shape life-style data structure 336 further comprises (ii) a corresponding first intensity indicator, configured for displaying a first visual property of a single-shape life-style polygon 337, in the displayed mode. The method further comprises, for each respective time window 234, a step of creating a set of life-style data records 340, and thereby creating a plurality of sets of life-style data records, wherein each respective set of life-style data records 348 comprises a number of life-style data records 331 from the third data set 330, and wherein each respective life-style data record 331 within the respective set of life-style data records 348 have a life-style event timestamp 334 in the respective time window 234. The method further comprises, for each respective life-style data record 331, within each set of life-style data records 348 of the plurality of sets of life-style data records, a step of assigning a corresponding relative life-style time 349 being the relative time within the time window, whereby the plurality of sets of life-style data records represents the distribution of life-style related events. The method further comprises, for each respective set of life-style data records 348, a step of superimposing the single-shape life-style polygon 337 from each of the life-style data records 331 in the respective set of life-style data records 348, wherein the single-shape life-style polygon 337 is superimposed according to the first and the second dimension, wherein an interval along the first dimension is defined by the fixed duration of the time window 234, and whereby two or more superimposed single-shape life-style polygons may overlap within the interval. Responsive to identifying two or more superimposed overlapping single-shape life-style polygons, the method further comprises a step of creating a set of multi-shape life-style data structures 340, configured for representing the average and the variability of the distribution of life-style related events, in a displayed mode. The method further comprises, for each multi-shape life-style data structure 341, a step of (i) creating a corresponding subset of overlapping single-shape life-style polygons, wherein the subset of overlapping single-shape life-style polygons define a corresponding subset of single-shape life-style data structures (342), a step of (ii) calculating a corresponding multi-shape life-style polygon 244, configured for visualizing a polygon with a two-dimensional shape, in the displayed mode, wherein the multi-shape life-style polygon 344 is defined by the overlap between single-shape life-style polygons 337 of the corresponding subset of overlapping single-shape life-style data structures 342, a step of (iii) calculating the number of elements in the subset 345, being the sum of overlapping single-shape life-style data structures 336 in the subset of overlapping single shape life-style polygons 342, and a step of (iv) calculating a corresponding second life-style intensity indicator 346, configured for displaying a first visual property of the multi-shape life-style polygon 344, in the displayed mode, wherein the second life-style intensity indicator 346 is an increasing function of the number of single-shape life-style polygons 345. Therefore the display data 247 further comprises the plurality of sets of life-style data records, and the set of multi-shape life-style data structures 340, and the communication is directed to (i) the subject or (ii) to a health care provider for providing the life-style event history representing the average and the variability of the distribution of the life-style related events.

In some embodiments, each of the life-style data records 331 in the plurality of life-style data records further comprises (iii) a quantity of impact 333 representing the influence imposed by the life-style event on the subject's blood glucose level. In such embodiments, the corresponding single-shape life-style polygon 337 is further configured to be displayed with a second length extending in the second dimension, wherein the second length is having a fixed value or is variable and represents the quantity representing the influence on the subject's blood glucose level, whereby the set of multi-shape life-style data structures 340 is further configured for representing distributions relating to quantifiable life-style events.

In some embodiments, each of the life-style data records 331 in the plurality of life-style data records further comprises a corresponding type of life-style event 319 representing the type of event the subject engaged in. In such embodiments, the corresponding single-shape life-style data structure further comprises a corresponding first type of life-style event indicator 339, configured for displaying a second visual property of the single-shape life-style polygon 337, and thereby indicating the type of life-style event engaged in by the subject. In these embodiments, each of the single-shape life-style data structures 336 within the corresponding subset of single-shape life-style data structures 342 are having the same type of life-style event indicator 339, thereby indicating that they relate to the same type of life-style event engaged in by the subject. In such embodiments, each multi-shape life-style data structure 341 within the set of multi-shape life-style data structures 340 further comprises a second life-style event indicator 347 defined by the type of life-style event indicator 339 of the corresponding subset of single-shape life-style data structures (342). Furthermore, the second type of life-style event indicator, is configured for displaying a second visual property of the multi-shape life-style polygon 344, and thereby indicating the type of life-style event, which the subject has engaged in, whereby the set of multi-shape life-style data structure 340 is further configured for representing distributions relating to different types of life-style events.

LIST OF EMBODIMENTS

1. A device 250 for communicating a dose history configured for representing an average and a variability of a distribution of injections with a blood glucose regulating medicament applied by a subject with a treatment regimen;
the device comprises one or more processors 274 and a memory 192/290, the memory storing instructions that, when executed by the one or more processors, perform a method of:
obtaining a first data set 220 from one or more injection devices used by the subject to apply the treatment regimen, the first data set comprising a plurality of medicament records taken over a time course, each respective medicament record 222 in the plurality of medicament records comprising:
(i) a respective medicament injection event 224 including an amount of medicament 226 injected into the subject using a respective injection device 104 in the one or more injection devices,
(ii) a corresponding electronic injection event timestamp 229 within the time course that is automatically generated by the respective injection device upon occurrence of the respective medicament injection event 224;
wherein each of the medicament records 222 are assigned:
a corresponding single-shape data structure 230, configured for representing a single injection in the distribution of injections, in a displayed mode 260, wherein the single-shape data structure 230 comprises:
(i) a corresponding single-shape polygon 231, configured for visualizing a polygon 261 with a two-dimensional shape, in the displayed mode, wherein the single-shape polygon 231 is configured to be displayed with:
a first length 262 extending in the first dimension, wherein (i) the first length 262 is having a fixed value, or (ii) wherein the first length (262) is variable and represents a duration wherein the medicament relating to the respective medicament injection event 224 is still active, and
a second length 263 extending in the second dimension, wherein (i) the second length 263 is having a fixed value, or (ii) wherein the second length (262) is variable and represents an amount of injected medicament, or (iii) wherein the second length 262 is variable and represents an amount of active medicament remaining from the injected amount of medicament;
(ii) a corresponding first intensity indicator 232, configured for displaying a first visual property (264) of the single-shape polygon 261, in the displayed mode 260;
creating a plurality of consecutive time windows 233 within the time course, wherein each time window 234 is of the same fixed duration,
for each respective time window 234, creating a set of medicament records 235, and thereby creating a plurality of sets of medicament records, wherein each respective set of medicament records 235 comprises a number of medicament records from the first data set 220, and wherein each respective medicament record 222 within the respective set of medicament records (235) have a timestamp (229) in the respective time window 234;
for each respective medicament record 222, within each set of medicament records 235 of the plurality of sets of medicament records, assigning a corresponding relative time 237 being the relative time within the time window 234, whereby the plurality of sets of medicament records represents the distribution of injections;
for each respective set of medicament records 235, superimposing the single-shape polygon 231 from each of the medicament records 224 in the respective set of medicament records 235, wherein the single-shape polygon 231 is superimposed according to the first and the second dimension, wherein an interval along the first dimension is defined by the fixed duration of the time window, and whereby two or more superimposed single-shape polygons 231 may overlap within the interval;
responsive to identifying two or more superimposed overlapping single-shape polygons 231:
creating a set of multi-shape data structures 240, comprising a number of multi-shape data structures 241 configured for representing the average and the variability of the distribution of injections, in a displayed mode 260,
for each multi-shape data structure 241:
(i) creating a corresponding subset of overlapping single-shape polygons 542, wherein the subset of overlapping single-shape polygons 542 define a corresponding subset of single-shape data structures 242,
(ii) calculating a corresponding multi-shape polygon 244, configured for visualizing a polygon 265 with a two-dimensional shape, in the displayed mode 260, wherein the multi-shape polygon 244 is defined by the overlap between the single-shape polygons 231 of the corresponding subset of overlapping single-shape polygons 542, which corresponds to the subset of single-shape data structures 242,
(iii) calculating the number of elements in the subset 245, being the number of overlapping single-shape data structures 230 in the subset of overlapping single shape polygons 242,
(iv) calculating a corresponding second intensity indicator 246, configured for displaying the first visual property 264 of the multi-shape polygon 231, in the displayed mode, wherein the second intensity indicator 246 is an increasing function of the number of elements in the subset 245; and
communicating display data 247, wherein the display data 247 comprises:
(i) the plurality of sets of medicament records, and (ii) the set of multi-shape data structures (240); and wherein the communication is directed to (i) the subject or (ii) to a health care provider for providing the dose history representing the average and the variability of the distribution of the injections.

2. The device according to embodiment 1, wherein the treatment regimen comprises a bolus insulin medicament dosage regimen (208) with a short acting insulin medicament (210) and a basal insulin medicament dosage regimen (212) with a long acting insulin medicament (214).

3. The device according to any of embodiments 1 or 2, wherein the device further comprises a display (282), and wherein the step of communicating display data (247) further comprises:

displaying the display data (247) in a first coordinate system (380) on the display (282), wherein a first coordinate axis (381) is defined by the first dimension, and the second coordinate axis (382) is defined by the second dimension:

wherein each respective medicament record (222), in each respective set of medicament records (235), in each of the plurality of sets of medicament records, is displayed by arranging the corresponding single-shape polygon (231) in the first coordinate system (380) according to the corresponding relative time 237 and the corresponding amount of medicament (226), and wherein the visual property (264) of the single-shape polygon has been defined by the corresponding first intensity indicator (232); and wherein each respective multi-shape data structure (241), in the set of multi-shape data structures (240), is displayed by arranging the corresponding multi-shape polygon (244) in the first coordinate system (380), according to a position defined by the subset of overlapping single-shape polygons (542), and wherein the first visual property (264) of the multi-shape polygon (244) has been defined by the corresponding second intensity indicator (246).

4. The device according to any of the embodiments 1-2, wherein each respective medicament record (222) in the plurality of medicament records further comprises:

(iii) a corresponding type of medicament (228) injected into the subject; and wherein the single-shape data structure (232) corresponding to the respective medicament record (222) further comprises:

(iii) a corresponding type of medicament indicator (248), configured for displaying a second visual property (266) of the single-shape polygon (231), and thereby indicating the type of medicament (228) injected into the subject; and wherein each of the single-shape data structures (230) within the corresponding subset of single-shape data structures (242) are having the same type of medicament indicator (248), thereby indicating that they relate to injections with the same type of medicament (228); and wherein each multi-shape data structure (241) within the set of multi-shape data structures (240) further comprises a second type of medicament indicator (249) defined by the type of medicament indicator (248) of the corresponding subset of single-shape data structures, and wherein the second type of medicament indicator, is configured for displaying the second visual property (266) of the multi-shape polygon, and thereby indicating the type of medicament (228) injected into the subject, whereby the set of multi-shape data structures (240) is further configured for representing distributions relating to injections with different types of medicament.

5. The device according to embodiment 4, wherein the device further comprises a display (288), and wherein the step of communicating display data further comprises:

displaying the display data (247) in a first coordinate system (380) on the display (288), wherein a first coordinate axis (381) is defined by the first dimension, and the second coordinate axis (382) is defined by the second dimension:

wherein each respective medicament record (222), in each respective set of medicament records (235), in the plurality of sets of medicament records, is displayed by arranging each of the single-shape polygons (231) corresponding to the respective medicament record (222) in the coordinate system (380) according to the corresponding relative time 237 and the corresponding amount of medicament (226), and wherein the first visual appearance has been defined by the first intensity indicator (232) and the second visual appearance (266) has been defined by the first type of medicament indicator (248), wherein both indicators are corresponding to the respective medicament record (222); and wherein each respective multi-shape data structure (241), in the set of multi-shape data structures (240), is displayed by arranging each of the multi-shape polygons (244) corresponding to the respective multi-shape data structure (241) in the coordinate system (380), according to a position defined by the subset of overlapping single-shape polygons (542), and wherein the first visual appearance (264) has been defined by the second intensity indicator (246) and the second visual appearance (266) has been defined by the second type of medicament indicator (249).

6. The device according to any of embodiments 3 and 5, wherein the display (288) further comprises a second coordinate system (385) comprising a first axis (386) and a second axis (387), and wherein the second coordinate system represents an average and a variability of a distribution based on glucose data obtained within the time course, and wherein, for the first coordinate system (380), the second axis (382) represents the amount of injected medicament (226), and wherein, for the second coordinate system (385), the second axis (387) represents a blood glucose concentration, and wherein the first axis (381, 386) of both coordinate systems (380, 385) represent the time and are defined within the interval defined by the time window (234), and wherein the first axis (381, 386) of both coordinate systems (380, 385) have been arranged in parallel on top of each other or with an off-set in the direction of the second axis (382, 387), and wherein the second axis (382, 387) of both coordinate systems (380, 385) have been arranged in parallel.

7. The device according to any of the previous embodiments, wherein the single-shape polygon (231) is configured for visualizing a polygon (261) with a two-dimensional shape defining a circle, and wherein the second length (263) is having a fixed value.

8. The device according to any of the embodiments 1-5, and 7, wherein the method further comprises:

obtaining a second data set (310), wherein the second data set (310) comprises a plurality of autonomous glucose measurements of the subject within the time course and, for each respective autonomous glucose measurement (311) in the plurality of autonomous glucose measurements, a glucose measurement timestamp (312) representing when the respective measurement was made; and for each respective time window (234), creating a set of glucose measurements (315), and thereby creating a plurality of sets of glucose measurements, and wherein each glucose measurement (311) within the respective set of glucose measurements (315) have a timestamp (312) in the respective time window (234);

for each respective glucose measurement (311), associating a corresponding relative time (313) being the relative time within the time window, whereby the plurality of sets of glucose measurements are representing a distribution of glucose measurements within the time window;

calculating, for the plurality of sets of glucose measurements, the average and the variability as a function of the relative time, wherein the display data further comprises the plurality of sets of glucose measurements, the corresponding relative time, and the calculated average and the variability as a function of the relative time.

9. The device according to any of the previous embodiments, further adapted for communicating a life-style event history representing an average and a variability of a distribution of life-style related events within the time course, which the subject has engaged in, wherein the method further comprises:

obtaining a third data set (330) from one or more wearable life-style measurement devices (103) used by the subject to acquire life-style data, the third data set (330) comprises a plurality of life-style data records (331) over the time course, each respective life-style data record (331) in the plurality of life-style data records comprises:
(i) a respective life-style event (332),
(ii) a corresponding electronic life-style event timestamp (334) within the time course that is automatically generated by the respective life-style measurement device (103) upon occurrence of the respective life-style related event, or by user actuation of the respective life-style measurement device, or a begin timestamp and an end timestamp indicating the beginning and the ending time of the life-style event engaged in by the subject;

wherein each of the life-style data records (331) are assigned:
a corresponding single-shape life-style data structure (336), configured for representing a single event in the distribution of life-style related events, wherein the single-shape life-style data structure (336) comprises:
(i) a corresponding single-shape life-style polygon (337), configured for visualizing a polygon with a two-dimensional shape in the displayed mode, wherein the single-shape life-style polygon (337) is configured to be displayed with:
a first length extending in the first dimension, wherein the first length is having a fixed value, or is representing a duration of the life-style event the subject engaged in based on a response to an indication of that a begin time stamp and an end timestamp has been recorded, and
a second length extending in the second dimension;
(ii) a corresponding first intensity indicator, configured for displaying a first visual property of a single-shape life-style polygon (337), in the displayed mode;

for each respective time window (234), creating a set of life-style data records (340), and thereby creating a plurality of sets of life-style data records, wherein each respective set of life-style data records (348) comprises a number of life-style data records (331) from the third data set (330), and wherein each respective life-style data record (331) within the respective set of life-style data records (348) have a life-style event timestamp (334) in the respective time window (234);

for each respective life-style data record (331), within each set of life-style data records (348) of the plurality of sets of life-style data records, assigning a corresponding relative life-style time (349) being the relative time within the time window, whereby the plurality of sets of life-style data records represents the distribution of life-style related events;

for each respective set of life-style data records (348), superimposing the single-shape life-style polygon (337) from each of the life-style data records (331) in the respective set of life-style data records (348), wherein the single-shape life-style polygon (337) is superimposed according to the first and the second dimension, wherein an interval along the first dimension is defined by the fixed duration of the time window (234), and whereby two or more superimposed single-shape life-style polygons may overlap within the interval;

responsive to identifying two or more superimposed overlapping single-shape life-style polygons:

creating a set of multi-shape life-style data structures (340), configured for representing the average and the variability of the distribution of life-style related events, in a displayed mode, for each multi-shape life-style data structure (341):
(i) creating a corresponding subset of overlapping single-shape life-style polygons, wherein the subset of overlapping single-shape life-style polygons define a corresponding subset of single-shape life-style data structures (342),
(ii) calculating a corresponding multi-shape life-style polygon (244), configured for visualizing a polygon with a two-dimensional shape, in the displayed mode, wherein the multi-shape life-style polygon (344) is defined by the overlap between single-shape life-style polygons (337) of the corresponding subset of overlapping single-shape life-style data structures (342),
(iii) calculating the number of elements in the subset (345), being the sum of overlapping single-shape life-style data structures (336) in the subset of overlapping single shape life-style polygons (342),
(iv) calculating a corresponding second life-style intensity indicator (346), configured for displaying a first visual property of the multi-shape life-style polygon (344), in the displayed mode, wherein the second life-style intensity indicator (346) is an increasing function of the number of single-shape life-style polygons (345); and wherein the display data (247) further comprises:
the plurality of sets of life-style data records, and the set of multi-shape life-style data structures (340); and wherein
the communication is directed to (i) the subject or (ii) to a health care provider for providing the life-style event history representing the average and the variability of the distribution of the life-style related events.

10. The device according to embodiment 9, wherein each of the life-style data records (331) in the plurality of life-style data records further comprises:
   (iii) a quantity of impact (333) representing the influence imposed by the life-style event on the subject's blood glucose level; and
   wherein the corresponding single-shape life-style polygon (337) is further configured to be displayed with:
      a second length extending in the second dimension, wherein the second length is having a fixed value or is variable and represents the quantity representing the influence on the subject's blood glucose level, whereby the set of multi-shape life-style data structures (340) is further configured for representing distributions relating to quantifiable life-style events.

11. The device according to any of embodiments 9-10, wherein each of the life-style data records (331) in the plurality of life-style data records further comprises:
   (iii) a corresponding type of life-style event (319) representing the type of event the subject engaged in; and
   wherein the corresponding single-shape life-style data structure further comprises:
   (iii) a corresponding first type of life-style event indicator (339), configured for displaying a second visual property of the single-shape life-style polygon (337), and thereby indicating the type of life-style event engaged in by the subject; and wherein each of the single-shape life-style data structures (336) within the corresponding subset of single-shape life-style data structures (342) are having the same type of life-style event indicator (339), thereby indicating that they relate to the same type of life-style event engaged in by the subject, and wherein each multi-shape life-style data structure (341) within the set of multi-shape life-style data structures (340) further comprises a second life-style event indicator (347) defined by the type of life-style event indicator (339) of the corresponding subset of single-shape life-style data structures (342), and
   wherein the second type of life-style event indicator, is configured for displaying a second visual property of the multi-shape life-style polygon (344), and thereby indicating the type of life-style event, which the subject has engaged in, whereby the set of multi-shape life-style data structure (340) is further configured for representing distributions relating to different types of life-style events.

12. The device according to embodiment 1, wherein the treatment regimen (206) comprises a GLP-1 receptor agonist dosage regimen (216), with a medicament comprising a GLP-1 receptor agonist.

13. A method for communicating a dose event history representing an average and a variability of a distribution of injections with a blood glucose regulating medicament applied by a subject with a treatment regimen;
   using a device comprising one or more processors (274) and a memory (192/290), the memory storing instructions that, when executed by the one or more processors, perform a method of:
      obtaining a first data set (220) from one or more injection devices used by the subject to apply the treatment regimen, the first data set comprising a plurality of medicament records taken over a time course, each respective medicament record (222) in the plurality of medicament records comprising:
         (i) a respective medicament injection event (224) including an automatically obtained amount of medicament (226) injected into the subject using a respective injection device (104) in the one or more injection devices,
         (ii) a corresponding automatically obtained injection event timestamp (229) within the time course that is automatically generated by the respective injection device upon occurrence of the respective medicament injection event (224);
      wherein each of the medicament records (222) are assigned:
         a corresponding single-shape data structure (230), configured for representing a single injection in the distribution of injections, in a displayed mode (260), wherein the single-shape data structure (230) comprises:
            (i) a corresponding single-shape polygon (231), configured for visualizing a polygon (261) with a two-dimensional shape, in the displayed mode, wherein the single-shape polygon (231) is configured to be displayed with:
               a first length (262) extending in the first dimension, and with first a coordinate according to the first dimension, wherein (i) the first length (262) is having a fixed value, or (ii) wherein the first length (262) is variable and represents a duration wherein the medicament relating to the respective medicament injection event (224) is still active, and
               a second length (263) extending in the second dimension, and with a second coordinate according to the second dimension, wherein (i) the second length (263) is having a fixed value, or (ii) wherein the second length (262) is variable and represents an amount of injected medicament, or (iii) wherein the second length (262) is variable and represents an amount of active medicament remaining from the injected amount of medicament;
            (ii) a corresponding first intensity indicator (232), configured for displaying a first visual property (264) of the single-shape polygon (261), in the displayed mode (260);
      creating a plurality of consecutive time windows (233) within the time course, wherein each time window (234) is of the same fixed duration,
      for each respective time window (234), creating a set of medicament records (235), and thereby creating a plurality of sets of medicament records, wherein each respective set of medicament records 235 comprises a number of medicament records from the first data set (220), and wherein each respective medicament record (222) within the respective set of medicament records (235) have a timestamp (229) in the respective time window (234);
      for each respective medicament record (222), within each set of medicament records (235) of the plurality of sets of medicament records, assigning a corresponding relative time (237) being the relative time within the time window (234), whereby the plurality of sets of medicament records represents the distribution of injections;
      for each respective set of medicament records (235), superimposing the single-shape polygon (231) from each of the medicament records (224) in the respective set of medicament records (235), wherein the single-shape polygon (231) is superimposed according to the first dimension being the relative time and the second dimension being the amount of injected medicament, wherein an interval along the first dimension is defined by the fixed duration of the time window, and whereby two or more superimposed single-shape polygons (231) may overlap within the interval;

responsive to identifying two or more superimposed overlapping single-shape polygons (231):

creating a set of multi-shape data structures (240), comprising a number of multi-shape data structures (241) configured for representing the average and the variability of the distribution of injections, in a displayed mode (260), for each multi-shape data structure (241):
  (i) creating a corresponding subset of overlapping single-shape polygons (542), wherein the subset of overlapping single-shape polygons (542) define a corresponding subset of single-shape data structures (242),
  (ii) calculating a corresponding multi-shape polygon (244), configured for visualizing a polygon (265) with a two-dimensional shape and according to the first and the second dimension, in the displayed mode (260), wherein the multi-shape polygon (244) is defined by the overlap between the single-shape polygons (231) of the corresponding subset of overlapping single-shape polygons (542), which corresponds to the subset of single-shape data structures (242),
  (iii) calculating the number of elements in the subset (245), being the number of overlapping single-shape data structures (230) in the subset of overlapping single shape polygons (242),
  (iv) calculating a corresponding second intensity indicator (246), configured for displaying the first visual property (264) of the multi-shape polygon (231), in the displayed mode, wherein the second intensity indicator (246) is an increasing function of the number of elements in the subset (245); and communicating display data (247), wherein the display data (247) comprises:
  (i) the plurality of sets of medicament records, and
  (ii) the set of multi-shape data structures (240); and wherein the communication is directed to (i) the subject or (ii) to a health care provider for providing the dose history representing the average and the variability of the distribution of the injections.

14. A computer program comprising instructions that, when executed by one or more processors, perform the method of:

obtaining a first data set (220) from one or more injection devices used by the subject to apply the treatment regimen, the first data set comprising a plurality of medicament records taken over a time course, each respective medicament record (222) in the plurality of medicament records comprising:
  (i) a respective medicament injection event (224) including an automatically obtained amount of medicament (226) injected into the subject using a respective injection device (104) in the one or more injection devices,
  (ii) a corresponding automatically obtained injection event timestamp (229) within the time course that is automatically generated by the respective injection device upon occurrence of the respective medicament injection event (224);

wherein each of the medicament records (222) are assigned:
  a corresponding single-shape data structure (230), configured for representing a single injection in the distribution of injections, in a displayed mode (260), wherein the single-shape data structure (230) comprises:
    (i) a corresponding single-shape polygon (231), configured for visualizing a polygon (261) with a two-dimensional shape, in the displayed mode, wherein the single-shape polygon (231) is configured to be displayed with:
      a first length (262) extending in the first dimension, and with first a coordinate according to the first dimension, wherein (i) the first length (262) is having a fixed value, or (ii) wherein the first length (262) is variable and represents a duration wherein the medicament relating to the respective medicament injection event (224) is still active, and
      a second length (263) extending in the second dimension, and with a second coordinate according to the second dimension, wherein (i) the second length (263) is having a fixed value, or (ii) wherein the second length (262) is variable and represents an amount of injected medicament, or (iii) wherein the second length (262) is variable and represents an amount of active medicament remaining from the injected amount of medicament;
    (ii) a corresponding first intensity indicator (232), configured for displaying a first visual property (264) of the single-shape polygon (261), in the displayed mode (260);

creating a plurality of consecutive time windows (233) within the time course, wherein each time window (234) is of the same fixed duration,
  for each respective time window (234), creating a set of medicament records (235), and thereby creating a plurality of sets of medicament records, wherein each respective set of medicament records 235 comprises a number of medicament records from the first data set (220), and wherein each respective medicament record (222) within the respective set of medicament records (235) have a timestamp (229) in the respective time window (234);

for each respective medicament record (222), within each set of medicament records (235) of the plurality of sets of medicament records, assigning a corresponding relative time (237) being the relative time within the time window (234), whereby the plurality of sets of medicament records represents the distribution of injections;

for each respective set of medicament records (235), superimposing the single-shape polygon (231) from each of the medicament records (224) in the respective set of medicament records (235), wherein the single-shape polygon (231) is superimposed according to the first dimension being the relative time and the second dimension being the amount of injected medicament, wherein an interval along the first dimension is defined by the fixed duration of the time window, and whereby two or more superimposed single-shape polygons (231) may overlap within the interval;

responsive to identifying two or more superimposed overlapping single-shape polygons (231):

creating a set of multi-shape data structures (240), comprising a number of multi-shape data structures (241) configured for representing the average and the variability of the distribution of injections, in a displayed mode (260), for each multi-shape data structure (241):
(i) creating a corresponding subset of overlapping single-shape polygons (542), wherein the subset of overlapping single-shape polygons (542) define a corresponding subset of single-shape data structures (242),
(ii) calculating a corresponding multi-shape polygon (244), configured for visualizing a polygon (265) with a two-dimensional shape and according to the first and the second dimension, in the displayed mode (260), wherein the multi-shape polygon (244) is defined by the overlap between the single-shape polygons (231) of the corresponding subset of overlapping single-shape polygons (542), which corresponds to the subset of single-shape data structures (242),
(iii) calculating the number of elements in the subset (245), being the number of overlapping single-shape data structures (230) in the subset of overlapping single shape polygons (242),
(iv) calculating a corresponding second intensity indicator (246), configured for displaying the first visual property (264) of the multi-shape polygon (231), in the displayed mode, wherein the second intensity indicator (246) is an increasing function of the number of elements in the subset (245); and communicating display data (247), wherein the display data (247) comprises:
(i) the plurality of sets of medicament records, and
(ii) the set of multi-shape data structures (240); and wherein the communication is directed to a display (282).

15. A computer-readable data carrier having stored thereon the computer program according to embodiment 14.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIGS. 1, 2, 3 and/or described in FIG. 4. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

The invention claimed is:

1. A device for communicating a dose history configured for representing an average and a variability of a distribution of injections with a blood glucose regulating medicament applied by a subject with a treatment regimen;
the device comprises one or more processors and a memory, the memory storing instructions that, when executed by the one or more processors, perform a method of:
obtaining a first data set from one or more injection devices used by the subject to apply the treatment regimen, the first data set comprising a plurality of medicament records taken over a time course, each respective medicament record in the plurality of medicament records comprising:
(i) a respective medicament injection event including an automatically obtained amount of medicament injected into the subject using a respective injection device in the one or more injection devices,
(ii) a corresponding automatically obtained injection event timestamp within the time course that is automatically generated by the respective injection device upon occurrence of the respective medicament injection event;
wherein each of the medicament records are assigned:
a corresponding single-shape data structure, configured for representing a single injection in the distribution of injections, in a displayed mode, wherein the single-shape data structure comprises:
(i) a corresponding single-shape polygon, configured for visualizing a polygon with a two-dimensional shape, in the displayed mode, wherein the single-shape polygon is configured to be displayed with:
a first length extending in a first dimension, and with first a coordinate according to the first dimension, wherein (i) the first length is having a fixed value, or (ii) wherein the first length is variable and represents a duration wherein the medicament relating to the respective medicament injection event is still active, and
a second length extending in a second dimension, and with a second coordinate according to the second dimension, wherein (i) the second length is having a fixed value, or (ii) wherein the second length is variable and represents an amount of injected medicament, or (iii) wherein the second length is variable and represents an amount of active medicament remaining from the injected amount of medicament;
(ii) a corresponding first intensity indicator, configured for displaying a first visual property of the single-shape polygon, in the displayed mode;
creating a plurality of consecutive time windows within the time course, wherein each time window is of the same fixed duration,
for each respective time window, creating a set of medicament records, and thereby creating a plurality of sets of medicament records, wherein each respective set of medicament records comprises a number of medicament records from the first data set, and wherein each respective medicament record within the respective set of medicament records have a timestamp in the respective time window;
for each respective medicament record, within each set of medicament records of the plurality of sets of medicament records, assigning a corresponding relative time being the relative time within the time window, whereby the plurality of sets of medicament records represents the distribution of injections;

for each respective set of medicament records, superimposing the single-shape polygon from each of the medicament records in the respective set of medicament records, wherein the single-shape polygon is superimposed according to the first dimension being the relative time and the second dimension being the amount of injected medicament, wherein an interval along the first dimension is defined by the fixed duration of the time window, and whereby two or more superimposed single-shape polygons may overlap within the interval;

responsive to identifying two or more superimposed overlapping single-shape polygons:

creating a set of multi-shape data structures, comprising a number of multi-shape data structures configured for representing the average and the variability of the distribution of injections, in a displayed mode, for each multi-shape data structure:
 (i) creating a corresponding subset of overlapping single-shape polygons, wherein the subset of overlapping single-shape polygons define a corresponding subset of single-shape data structures,
 (ii) calculating a corresponding multi-shape polygon, configured for visualizing a polygon with a two-dimensional shape and according to the first and the second dimension, in the displayed mode, wherein the multi-shape polygon is defined by the overlap between the single-shape polygons of the corresponding subset of overlapping single-shape polygons, which corresponds to the subset of single-shape data structures,
 (iii) calculating a number of elements in the subset, being the number of overlapping single-shape data structures in the subset of overlapping single shape polygons,
 (iv) calculating a corresponding second intensity indicator, configured for displaying the first visual property of the multi-shape polygon, in the displayed mode, wherein the second intensity indicator is an increasing function of the number of elements in the subset; and communicating display data, wherein the display data comprises:
 (i) the plurality of sets of medicament records, and
 (ii) the set of multi-shape data structures; and wherein the communication of the display data is directed to (i) the subject or (ii) to a health care provider for providing the dose history representing the average and the variability of the distribution of the injections.

2. The device according to claim 1, wherein the treatment regimen comprises a bolus insulin medicament dosage regimen with a short acting insulin medicament and a basal insulin medicament dosage regimen with a long acting insulin medicament.

3. The device according to claim 1, wherein the device further comprises a display, and wherein the step of communicating display data further comprises:
 displaying the display data in a first coordinate system on the display, wherein a first coordinate axis is defined by the first dimension, and the second coordinate axis is defined by the second dimension:
  wherein each respective medicament record, in each respective set of medicament records, in the plurality of sets of medicament records, is displayed by arranging the corresponding single-shape polygon in the first coordinate system according to the corresponding relative time and the corresponding amount of medicament, and wherein the visual property of the single-shape polygon has been defined by the corresponding first intensity indicator; and
  wherein each respective multi-shape data structure, in the set of multi-shape data structures, is displayed by arranging the corresponding multi-shape polygon in the first coordinate system, according to a position defined by the subset of overlapping single-shape polygons, and wherein the first visual property of the multi-shape polygon has been defined by the corresponding second intensity indicator.

4. The device according to claim 1, wherein each respective medicament record in the plurality of medicament records further comprises:
 (iii) a corresponding type of medicament injected into the subject; and wherein the single-shape data structure corresponding to the respective medicament record further comprises:
 (iii) a corresponding type of medicament indicator, configured for displaying a second visual property of the single-shape polygon, and thereby indicating the type of medicament injected into the subject; and wherein each of the single-shape data structures within the corresponding subset of single-shape data structures are having the same type of medicament indicator, thereby indicating that they relate to injections with the same type of medicament; and wherein each multi-shape data structure within the set of multi-shape data structures further comprises a second type of medicament indicator defined by the type of medicament indicator of the corresponding subset of single-shape data structures, and wherein the second type of medicament indicator, is configured for displaying the second visual property of the multi-shape polygon, and thereby indicating the type of medicament injected into the subject, whereby the set of multi-shape data structures is further configured for representing distributions relating to injections with different types of medicament.

5. The device according to claim 4, wherein the device further comprises a display, and wherein the step of communicating display data further comprises:
 displaying the display data in a first coordinate system on the display, wherein a first coordinate axis is defined by the first dimension, and the second coordinate axis is defined by the second dimension:
  wherein each respective medicament record, in each respective set of medicament records, in the plurality of sets of medicament records, is displayed by arranging each of the single-shape polygons corresponding to the respective medicament record in the coordinate system according to the corresponding relative time and the corresponding amount of medicament, and wherein the first visual appearance has been defined by the first intensity indicator and the second visual appearance has been defined by the first type of medicament indicator, wherein both indicators are corresponding to the respective medicament record; and
  wherein each respective multi-shape data structure, in the set of multi-shape data structures, is displayed by arranging each of the multi-shape polygons corresponding to the respective multi-shape data structure in the coordinate system, according to a position defined by the subset of overlapping single-shape polygons, and wherein the first visual appearance has been defined by the second intensity indicator and the second visual appearance has been defined by the second type of medicament indicator.

6. The device according to claim 3, wherein the display further comprises a second coordinate system comprising a first axis and a second axis, and wherein the second coordinate system represents an average and a variability of a distribution based on glucose data obtained within the time course, and wherein, for the first coordinate system, the second axis represents the amount of injected medicament, and wherein, for the second coordinate system, the second axis represents a blood glucose concentration, and wherein the first axis of both coordinate systems represent the time and are defined within the interval defined by the time window, and wherein the first axis of both coordinate systems have been arranged in parallel on top of each other or with an off-set in the direction of the second axis, and wherein the second axis of both coordinate systems have been arranged in parallel.

7. The device according to claim 1, wherein the single-shape polygon is configured for visualizing a polygon with a two-dimensional shape defining a circle, and wherein the second length is having a fixed value.

8. The device according to claim 1, wherein the method further comprises:
obtaining a second data set, wherein the second data set comprises a plurality of autonomous glucose measurements of the subject within the time course and, for each respective autonomous glucose measurement in the plurality of autonomous glucose measurements, a glucose measurement timestamp representing when the respective measurement was made; and
for each respective time window, creating a set of glucose measurements, and thereby creating a plurality of sets of glucose measurements, and wherein each glucose measurement within the respective set of glucose measurements have a timestamp in the respective time window;
for each respective glucose measurement, associating a corresponding relative time being the relative time within the time window, whereby the plurality of sets of glucose measurements are representing a distribution of glucose measurements within the time window;
calculating, for the plurality of sets of glucose measurements, the average and the variability as a function of the relative time,
wherein the display data further comprises the plurality of sets of glucose measurements, the corresponding relative time, and the calculated average and the variability as a function of the relative time.

9. The device according to claim 1, further adapted for communicating a life-style event history representing an average and a variability of a distribution of life-style related events within the time course, which the subject has engaged in, wherein the method further comprises:
obtaining a third data set from one or more wearable life-style measurement devices used by the subject to acquire life-style data, the third data set comprises a plurality of life-style data records over the time course, each respective life-style data record in the plurality of life-style data records comprises:
(i) a respective life-style event,
(ii) a corresponding electronic life-style event timestamp within the time course that is automatically generated by the respective life-style measurement device upon occurrence of the respective life-style related event, or by user actuation of the respective life-style measurement device, or a begin timestamp and an end timestamp indicating the beginning and the ending time of the life-style event engaged in by the subject;
wherein each of the life-style data records are assigned:
a corresponding single-shape life-style data structure, configured for representing a single event in the distribution of life-style related events, wherein the single-shape life-style data structure comprises:
(i) a corresponding single-shape life-style polygon, configured for visualizing a polygon with a two-dimensional shape in the displayed mode, wherein the single-shape life-style polygon is configured to be displayed with:
a first length extending in the first dimension, wherein the first length is having a fixed value, or is representing a duration of the life-style event the subject engaged in based on a response to an indication of that a begin time stamp and an end timestamp has been recorded, and
a second length extending in the second dimension;
(ii) a corresponding first intensity indicator, configured for displaying a first visual property of a single-shape life-style polygon, in the displayed mode;
for each respective time window, creating a set of life-style data records, and thereby creating a plurality of sets of life-style data records, wherein each respective set of life-style data records comprises a number of life-style data records from the third data set, and wherein each respective life-style data record within the respective set of life-style data records have a life-style event timestamp in the respective time window;
for each respective life-style data record, within each set of life-style data records of the plurality of sets of life-style data records, assigning a corresponding relative life-style time being the relative time within the time window, whereby the plurality of sets of life-style data records represents the distribution of life-style related events;
for each respective set of life-style data records, superimposing the single-shape life-style polygon from each of the life-style data records in the respective set of life-style data records, wherein the single-shape life-style polygon is superimposed according to the first and the second dimension, wherein an interval along the first dimension is defined by the fixed duration of the time window, and whereby two or more superimposed single-shape life-style polygons may overlap within the interval;
responsive to identifying two or more superimposed overlapping single-shape life-style polygons:
creating a set of multi-shape life-style data structures, configured for representing the average and the variability of the distribution of life-style related events, in a displayed mode,
for each multi-shape life-style data structure:
(i) creating a corresponding subset of overlapping single-shape life-style polygons, wherein the subset of overlapping single-shape life-style polygons define a corresponding subset of single-shape life-style data structures,
(ii) calculating a corresponding multi-shape life-style polygon, configured for visualizing a polygon with a two-dimensional shape, in the displayed mode, wherein the multi-shape life-style polygon is defined by the overlap between single-shape life-style polygons of the corresponding subset of overlapping single-shape life-style data structures, (iii) calculating the number of elements in the subset, being the sum of overlapping single-shape life-style data structures in the subset of overlapping single shape life-style polygons, (iv) calculating a corresponding second life-style intensity indicator, configured for displaying a first visual property of the multi-shape life-style polygon, in the displayed mode, wherein the second life-style intensity indicator is an increasing function of the number of single-shape life-style polygons; and wherein the display data further comprises:

the plurality of sets of life-style data records, and the set of multi-shape life-style data structures; and wherein the communication is directed to (i) the subject or (ii) to a health care provider for providing the life-style event history representing the average and the variability of the distribution of the life-style related events.

10. The device according to claim 9, wherein each of the life-style data records in the plurality of life-style data records further comprises:

(iii) a quantity of impact representing the influence imposed by the life-style event on the subject's blood glucose level; and wherein the corresponding single-shape life-style polygon is further configured to be displayed with:

a second length extending in the second dimension, wherein the second length is having a fixed value or is variable and represents the quantity representing the influence on the subject's blood glucose level, whereby the set of multi-shape life-style data structures is further configured for representing distributions relating to quantifiable life-style events.

11. The device according to claim 9, wherein each of the life-style data records in the plurality of life-style data records further comprises:

a corresponding type of life-style event representing the type of event the subject engaged in; and wherein the corresponding single-shape life-style data structure further comprises:

a corresponding first type of life-style event indicator, configured for displaying a second visual property of the single-shape life-style polygon, and thereby indicating the type of life-style event engaged in by the subject; and wherein each of the single-shape life-style data structures within the corresponding subset of single-shape life-style data structures are having the same type of life-style event indicator, thereby indicating that they relate to the same type of life-style event engaged in by the subject, and wherein each multi-shape life-style data structure within the set of multi-shape life-style data structures further comprises a second life-style event indicator defined by the type of life-style event indicator of the corresponding subset of single-shape life-style data structures, and wherein the second type of life-style event indicator, is configured for displaying a second visual property of the multi-shape life-style polygon, and thereby indicating the type of life-style event, which the subject has engaged in, whereby the set of multi-shape life-style data structure is further configured for representing distributions relating to different types of life-style events.

12. The device according to claim 1, wherein the treatment regimen comprises a GLP-1 receptor agonist dosage regimen, with a medicament comprising a GLP-1 receptor agonist.

13. A method for communicating a dose event history representing an average and a variability of a distribution of injections with a blood glucose regulating medicament applied by a subject with a treatment regimen;

using a device comprising one or more processors and a memory, the memory storing instructions that, when executed by the one or more processors, perform a method of:

obtaining a first data set from one or more injection devices used by the subject to apply the treatment regimen, the first data set comprising a plurality of medicament records taken over a time course, each respective medicament record in the plurality of medicament records comprising:

(i) a respective medicament injection event including an automatically obtained amount of medicament injected into the subject using a respective injection device in the one or more injection devices, (ii) a corresponding automatically obtained injection event timestamp within the time course that is automatically generated by the respective injection device upon occurrence of the respective medicament injection event;

wherein each of the medicament records are assigned:

a corresponding single-shape data structure, configured for representing a single injection in the distribution of injections, in a displayed mode, wherein the single-shape data structure comprises:

(i) a corresponding single-shape polygon, configured for visualizing a polygon with a two-dimensional shape, in the displayed mode, wherein the single-shape polygon is configured to be displayed with:

a first length extending in a first dimension, and with first a coordinate according to the first dimension, wherein (i) the first length is having a fixed value, or (ii) wherein the first length is variable and represents a duration wherein the medicament relating to the respective medicament injection event is still active, and a second length extending in a second dimension, and with a second coordinate according to the second dimension, wherein (i) the second length is having a fixed value, or (ii) wherein the second length is variable and represents an amount of injected medicament, or (iii) wherein the second length is variable and represents an amount of active medicament remaining from the injected amount of medicament;

(ii) a corresponding first intensity indicator, configured for displaying a first visual property of the single-shape polygon, in the displayed mode;

creating a plurality of consecutive time windows within the time course, wherein each time window is of the same fixed duration, for each respective time window, creating a set of medicament records, and thereby creating a plurality of sets of medicament records, wherein each respective set of medicament records comprises a number of medicament records from the first data set, and wherein each respective medicament record within the respective set of medicament records have a timestamp in the respective time window;

for each respective medicament record, within each set of medicament records of the plurality of sets of medicament records, assigning a corresponding relative time being the relative time within the time window, whereby the plurality of sets of medicament records represents the distribution of injections;

for each respective set of medicament records, superimposing the single-shape polygon from each of the medicament records in the respective set of medicament records, wherein the single-shape polygon is superimposed according to the first dimension being the relative time and the second dimension being the amount of injected medicament, wherein an interval along the first dimension is defined by the fixed duration of the time window, and whereby two or more superimposed single-shape polygons may overlap within the interval;

responsive to identifying two or more superimposed overlapping single-shape polygons:

creating a set of multi-shape data structures, comprising a number of multi-shape data structures configured for representing the average and the variability of the distribution of injections, in a displayed mode, for each multi-shape data structure:

(i) creating a corresponding subset of overlapping single-shape polygons, wherein the subset of overlapping single-shape polygons define a corresponding subset of single-shape data structures, (ii) calculating a corresponding multi-shape polygon, configured for visualizing a polygon with a two-dimensional shape and according to the first and the second dimension, in the displayed mode, wherein the multi-shape polygon is defined by the overlap between the single-shape polygons of the corresponding subset of overlapping single-shape polygons, which corresponds to the subset of single-shape data structures, (iii) calculating a number of elements in the subset, being the number of overlapping single-shape data structures in the subset of overlapping single shape polygons, (iv) calculating a corresponding second intensity indicator, configured for displaying the first visual property of the multi-shape polygon, in the displayed mode, wherein the second intensity indicator is an increasing function of the number of elements in the subset; and communicating display data, wherein the display data comprises:

(i) the plurality of sets of medicament records, and (ii) the set of multi-shape data structures; and wherein the communication of the display data is directed to (i) the subject or (ii) to a health care provider for providing the dose history representing the average and the variability of the distribution of the injections.

14. A computer program comprising instructions that, when executed by one or more processors, perform the method of:

obtaining a first data set from one or more injection devices used by the subject to apply the treatment regimen, the first data set comprising a plurality of medicament records taken over a time course, each respective medicament record in the plurality of medicament records comprising:

(i) a respective medicament injection event including an automatically obtained amount of medicament injected into the subject using a respective injection device in the one or more injection devices, (ii) a corresponding automatically obtained injection event timestamp within the time course that is automatically generated by the respective injection device upon occurrence of the respective medicament injection event;

wherein each of the medicament records are assigned:

a corresponding single-shape data structure, configured for representing a single injection in the distribution of injections, in a displayed mode, wherein the single-shape data structure comprises:

(i) a corresponding single-shape polygon, configured for visualizing a polygon with a two-dimensional shape, in the displayed mode, wherein the single-shape polygon is configured to be displayed with:

a first length extending in a first dimension, and with first a coordinate according to the first dimension, wherein (i) the first length is having a fixed value, or (ii) wherein the first length is variable and represents a duration wherein the medicament relating to the respective medicament injection event is still active, and a second length extending in a second dimension, and with a second coordinate according to the second dimension, wherein (i) the second length is having a fixed value, or (ii) wherein the second length is variable and represents an amount of injected medicament, or (iii) wherein the second length is variable and represents an amount of active medicament remaining from the injected amount of medicament;

(ii) a corresponding first intensity indicator, configured for displaying a first visual property of the single-shape polygon, in the displayed mode;

creating a plurality of consecutive time windows within the time course, wherein each time window is of the same fixed duration, for each respective time window, creating a set of medicament records, and thereby creating a plurality of sets of medicament records, wherein each respective set of medicament records comprises a number of medicament records from the first data set, and wherein each respective medicament record within the respective set of medicament records have a timestamp in the respective time window;

for each respective medicament record, within each set of medicament records of the plurality of sets of medicament records, assigning a corresponding relative time being the relative time within the time window, whereby the plurality of sets of medicament records represents the distribution of injections;

for each respective set of medicament records, superimposing the single-shape polygon from each of the medicament records in the respective set of medicament records, wherein the single-shape polygon is superimposed according to the first dimension being the relative time and the second dimension being the amount of injected medicament, wherein an interval along the first dimension is defined by the fixed duration of the time window, and whereby two or more superimposed single-shape polygons may overlap within the interval;

responsive to identifying two or more superimposed overlapping single-shape polygons:

creating a set of multi-shape data structures, comprising a number of multi-shape data structures configured for representing the average and the variability of the distribution of injections, in a displayed mode, for each multi-shape data structure:

(i) creating a corresponding subset of overlapping single-shape polygons, wherein the subset of overlapping single-shape polygons define a corresponding subset of single-shape data structures, (ii) calculating a corresponding multi-shape polygon, configured for visualizing a polygon with a two-dimensional shape and according to the first and the second dimension, in the displayed mode, wherein the multi-shape polygon is defined by the overlap between the single-shape polygons of the corresponding subset of overlapping single-shape polygons, which corresponds to the subset of single-shape data structures, (iii) calculating a number of elements in the subset, being the number of overlapping single-shape data structures in the subset of overlapping single shape polygons, (iv) calculating a corresponding second intensity indicator, configured for displaying the first visual property of the multi-shape polygon, in the displayed mode, wherein the second intensity indicator is an increasing function of the number of elements in the subset; and communicating display data, wherein the display data comprises:

(i) the plurality of sets of medicament records, and (ii) the set of multi-shape data structures; and wherein the communication of the display data is directed to a display.

15. A computer-readable data carrier having stored thereon the computer program according to claim 14.

\* \* \* \* \*